(12) United States Patent
Hallak et al.

(10) Patent No.: US 8,206,909 B2
(45) Date of Patent: Jun. 26, 2012

(54) UNRESTRICTED MUTAGENESIS AND CLONING METHODS

(76) Inventors: Louay K Hallak, Columbus, OH (US); Mark E Peeples, Bexley, OH (US)

( * ) Notice: Subject to any disclaimer, the term of this patent is extended or adjusted under 35 U.S.C. 154(b) by 530 days.

(21) Appl. No.: 12/444,264

(22) PCT Filed: Oct. 4, 2007

(86) PCT No.: PCT/US2007/080493
§ 371 (c)(1),
(2), (4) Date: Apr. 3, 2009

(87) PCT Pub. No.: WO2008/067035
PCT Pub. Date: Jun. 5, 2008

(65) Prior Publication Data
US 2011/0256540 A1    Oct. 20, 2011

Related U.S. Application Data

(60) Provisional application No. 60/849,977, filed on Oct. 5, 2006.

(51) Int. Cl.
*C12Q 1/68* (2006.01)
(52) U.S. Cl. ........................................................ 435/6.1
(58) Field of Classification Search ........................ None
See application file for complete search history.

(56) References Cited

U.S. PATENT DOCUMENTS

| | | | |
|---|---|---|---|
| 6,261,797 B1 * | 7/2001 | Sorge et al. | 435/41 |
| 6,420,144 B1 * | 7/2002 | Chen et al. | 435/91.1 |
| 6,620,597 B1 * | 9/2003 | Chen et al. | 435/91.1 |
| 2006/0134624 A1 * | 6/2006 | Salerno | 435/6 |

FOREIGN PATENT DOCUMENTS

WO    WO 2005054435 A2 *    6/2005

* cited by examiner

*Primary Examiner* — Christopher M. Babic
(74) *Attorney, Agent, or Firm* — Calfee, Halter & Griswold LLP

(57) ABSTRACT

The invention relates to methods for amplifying, modifying, mutating and cloning DNA of any size. These methods comprise a series of PCR reactions, which are punctuated by ligation reactions.

27 Claims, 11 Drawing Sheets

Unrestricted Mutagenesis and Cloning (URMAC)

Figure 2: Insertion of DNA by Blunt End Ligation into Closed Starter DNA and Selection for the Orientation by PCR Continue as in Figure 1

Figure 4: URMAC Cloning via Large Opener Primer

Figure 5: URMAC scheme used to generate three M2 deletion mutants in the respiratory syncytial virus replicon cDNA.

Figure 7A
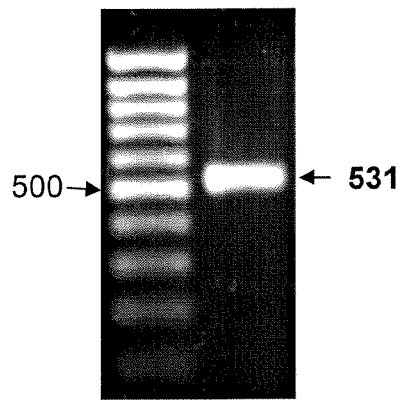
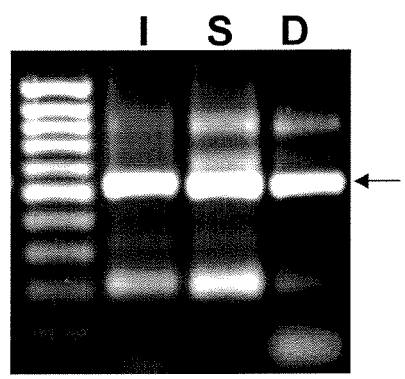
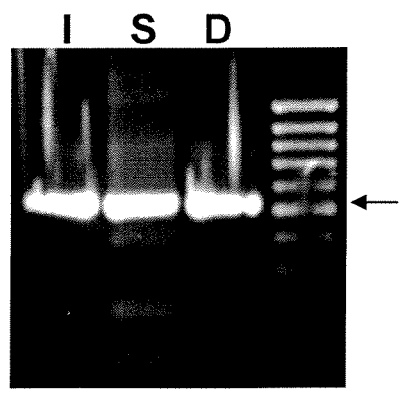

Figure 8. Modification of URMAC Starter Primers that makes the first URMAC ligation unnecessary: Oligo Instead of Ligation (OIL).
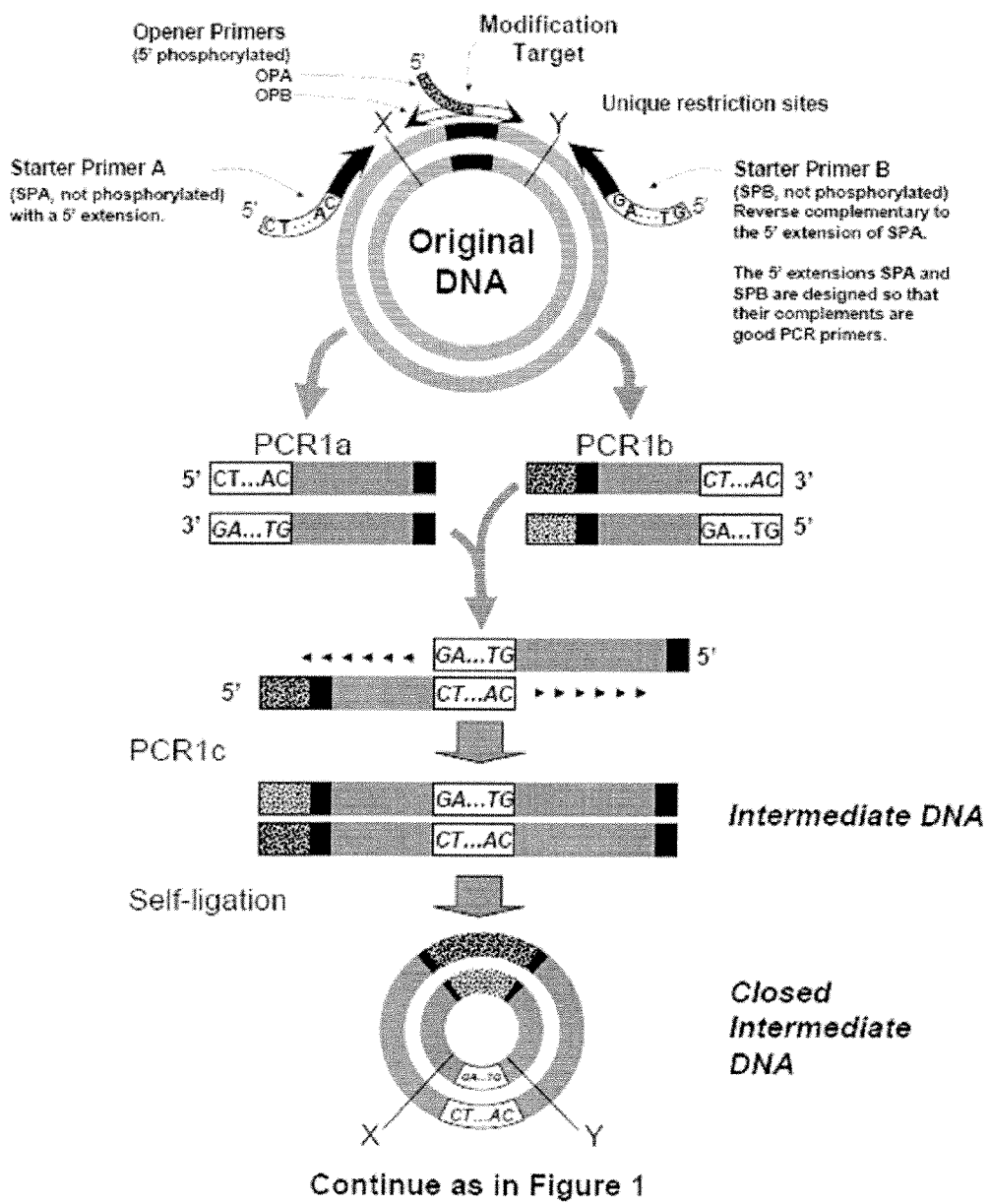

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Primer SP1

<400> SEQUENCE: 1
acttgtatcg tcgccatcgg                                            20

<210> SEQ ID NO 2
<211> LENGTH: 20
<212> TYPE: DNA
<213> ORGANISM: Artificial Sequence
<220> FEATURE:
<223> OTHER INFORMATION: Primer SP2

<400> SEQUENCE: 2
agaaacgtag tcctgataac                                            20

<210> SEQ ID NO 3
<211> LENGTH: 24
<212> TYPE: DNA
<213> ORGANISM: Artificial Sequence
<220> FEATURE:
```

<223> OTHER INFORMATION: OP1 Primer

<400> SEQUENCE: 3
atttgcccca gttttcattt ttac　　　　　　　　　　　　　　　　　　　24

<210> SEQ ID NO 4
<211> LENGTH: 28
<212> TYPE: DNA
<213> ORGANISM: Artificial Sequence
<220> FEATURE:
<223> OTHER INFORMATION: OP2 primer

<400> SEQUENCE: 4
caaatgacca tgccaaaaat aatgatac　　　　　　　　　　　　　　　　28

<210> SEQ ID NO 5
<211> LENGTH: 23
<212> TYPE: DNA
<213> ORGANISM: Artificial Sequence
<220> FEATURE:
<223> OTHER INFORMATION: OP3 primer

<400> SEQUENCE: 5
gtcaggtagt atcattattt ttg　　　　　　　　　　　　　　　　　　　23

<210> SEQ ID NO 6
<211> LENGTH: 25
<212> TYPE: DNA
<213> ORGANISM: Artificial Sequence
<220> FEATURE:
<223> OTHER INFORMATION: OP4 primer

<400> SEQUENCE: 6
caccacatcg ttacattatt aattc　　　　　　　　　　　　　　　　　25

<210> SEQ ID NO 7
<211> LENGTH: 20
<212> TYPE: DNA
<213> ORGANISM: Artificial Sequence
<220> FEATURE:
<223> OTHER INFORMATION: SP1 primer

<400> SEQUENCE: 7
acacatgcag ctcccggaga　　　　　　　　　　　　　　　　　　　　20

<210> SEQ ID NO 8
<211> LENGTH: 22
<212> TYPE: DNA
<213> ORGANISM: Artificial Sequence
<220> FEATURE:
<223> OTHER INFORMATION: SP2 primer

<400> SEQUENCE: 8
ctcactcatt aggcacccca gg　　　　　　　　　　　　　　　　　　22

<210> SEQ ID NO 9
<211> LENGTH: 22
<212> TYPE: DNA
<213> ORGANISM: Artificial Sequence
<220> FEATURE:
<223> OTHER INFORMATION: D> primer

<400> SEQUENCE: 9
cggtgtgaaa taccgcacag at　　　　　　　　　　　　　　　　　　22

<210> SEQ ID NO 10

```
<211> LENGTH: 22
<212> TYPE: DNA
<213> ORGANISM: Artificial Sequence
<220> FEATURE:
<223> OTHER INFORMATION: D< primer

<400> SEQUENCE: 10
gtgcactctc agtacaatct gc                                              22

<210> SEQ ID NO 11
<211> LENGTH: 22
<212> TYPE: DNA
<213> ORGANISM: Artificial Sequence
<220> FEATURE:
<223> OTHER INFORMATION: S> primer

<400> SEQUENCE: 11
cgtcggtgtg aaataccgca ca                                              22

<210> SEQ ID NO 12
<211> LENGTH: 22
<212> TYPE: DNA
<213> ORGANISM: Artificial Sequence
<220> FEATURE:
<223> OTHER INFORMATION: S< primer

<400> SEQUENCE: 12
cgtgtgcact ctcagtacaa tc                                              22

<210> SEQ ID NO 13
<211> LENGTH: 24
<212> TYPE: DNA
<213> ORGANISM: Artificial Sequence
<220> FEATURE:
<223> OTHER INFORMATION: I> primer

<400> SEQUENCE: 13
catatgcggt gtgaaatacc gcac                                            24

<210> SEQ ID NO 14
<211> LENGTH: 24
<212> TYPE: DNA
<213> ORGANISM: Artificial Sequence
<220> FEATURE:
<223> OTHER INFORMATION: I< primer

<400> SEQUENCE: 14
acgcgtgtgc actctcagta caat                                            24

<210> SEQ ID NO 15
<211> LENGTH: 40
<212> TYPE: DNA
<213> ORGANISM: Artificial Sequence
<220> FEATURE:
<223> OTHER INFORMATION: OIL Starter Primer A

<400> SEQUENCE: 15
cttacgggct agaggatgac acacatgcag ctcccggaga                           40

<210> SEQ ID NO 16
<211> LENGTH: 42
<212> TYPE: DNA
<213> ORGANISM: Artificial Sequence
<220> FEATURE:
<223> OTHER INFORMATION: OIL Starter Primer B
```

```
<400> SEQUENCE: 16
gtcatcctct agcccgtaag ctcactcatt aggcacccca gg                              42
```

UNRESTRICTED MUTAGENESIS AND CLONING METHODS

FIELD OF INVENTION

The invention described herein relates to methods for amplifying, modifying, mutating and cloning deoxyribonucleic acid (DNA) of any size. The basic methods of this invention comprise a series of polymerase chain reactions (PCR) punctuated by ligation reactions.

SEQUENCE LISTING

The instant application contains a Sequence Listing which has been submitted in ASCII format via EFS-Web and is hereby incorporated by reference in its entirety. Said ASCII copy, created on May 14, 2012, is named Unrestricted Mutagenesis_ST25.txt and is 4,096 bytes in size.

BACKGROUND

Mutagenesis of linear or circular DNA larger than five to eight kbp (kilobase pair) in size is a tedious and often slow process. Most mutagenesis technologies for such DNA require the availability of unique restriction enzyme sites flanking the region targeted for mutagenesis and numerous steps of DNA and bacterial handling. Some of these steps include excising a fragment of DNA that contains the mutagenesis target site along with a flanking region, hereafter referred to as the target-containing DNA fragment (TDF), using restriction enzyme(s), followed by inserting the TDF into a cloning plasmid which is usually less than five kbp in size. This step requires cleaving both the original plasmid containing the TDF and the cloning plasmid with restriction enzymes and subsequently ligating the TDF into the cloning plasmid.

The TDF-containing cloning plasmid is then transformed into bacterial cells, and the transformed bacteria are grown on selective solid medium to allow only those bacterial cells that successfully uptake the TDF-containing cloning DNA plasmid to grow into colonies. Not all colonies will contain the newly introduced TDF because some of the empty cloning plasmids can transform bacteria due to inefficiency in restriction enzyme cleavage. Therefore, several bacterial clones are picked from the solid medium plates and grown in liquid medium. Their DNA contents are extracted with chemical reagents and multiple purification steps are required to remove contaminating bacterial chromosomal DNA, RNA, proteins and carbohydrates. The extracted DNA is then analyzed by DNA sizing, restriction analysis or PCR methods to identify a correct TDF-containing clone. Once a correct bacterial clone is identified, it is amplified by growing it in a larger volume of bacterial growth liquid medium, harvested by centrifugation, lysed by chemical reagents, and its plasmid DNA content is extracted and purified. The actual mutagenesis steps are then performed on this plasmid DNA by conventional methods such as site-specific mutagenesis without phenotypic selection (Kunkel, *Proc Natl Acad Sci USA* 82(2): 488-92, 1985), inverted PCR (Byrappa et al., *Genome Res* 5(4), 404-7, 1995), the QuikChange XL site-directed mutagenesis kit (Stratagene, U.S. Pat. Nos. 5,789,166 and 5,932,419), or similar methods.

After completing the mutagenesis, a mutant clone must be identified by repeating the bacterial transformation, growth on solid medium, selection of colonies, growth in medium, and DNA purification. At this stage and depending on the nature of the introduced mutation, a DNA sequencing step is usually necessary to ensure that the selected clone contains the correct mutation. The correct clone is then grown in liquid bacterial growth medium followed by centrifugation to harvest the bacterial pellet, and the plasmid DNA is extracted. The authenticity of the resulting DNA is examined by restriction analysis using the same restriction enzyme(s) that was used to excise the TDF from the Original DNA and insert it into the cloning plasmid, or other restriction enzymes that result in a unique pattern. The mutated TDF is then cleaved out of a correct plasmid by restriction enzymes and separated from the cloning plasmid backbone. This separation step is usually performed on agarose or polyacrylamide gels in the presence of a fluorescent dye to visualize and physically collect the mutated TDF. Gel-purified, mutated TDF is then ligated to the Original plasmid that had been cleaved with the same restriction enzymes used to isolate the TDF and purified on agarose gel separately. Each of the steps described above is time consuming, laborious, and can be fraught with problems that slow the mutagenesis process.

There is a need to develop more efficient, economical and reliable methods for modifying large DNA accurately and with a minimum number of steps. The invention described below, Unrestricted Mutagenesis and Cloning (URMAC), avoids all of the steps described above for conventional mutagenesis methods until insertion of the mutated TDF into the Original DNA. Instead, URMAC depends on a series of PCR reactions, punctuated by ligation reactions. URMAC allows precise modification of linear or circular DNA of any size at any point. In its simplest form, URMAC uses two unique restriction sites flanking the TDF in the Original DNA that are in close enough proximity to each other so that a fragment containing these restriction sites can be amplified by PCR. In a variation of URMAC that employs homologous recombination, flanking restriction sites are not necessary.

SUMMARY OF INVENTION

Current mutagenesis methods allow relatively easy insertion, deletion, or substitution of DNA sequences in small plasmids by copying the entire plasmid using primers that alter the ends of the resulting linear DNA, then circularizing it. Similar manipulations in larger plasmids (>5-8 kbp) are more difficult since there is a practical limit to the size of plasmid that can be readily amplified by PCR. The present invention provides for methods of modifying a target DNA using the technique of Unrestricted Mutagenesis and Cloning (URMAC). This technique allows for rapid mutagenesis of large linear or circular DNA. The basic URMAC combines a series of two PCR and three ligation steps as biochemical reactions with an additional optional enrichment PCR reaction, thereby avoiding subcloning and multiple steps of bacterial and DNA handling. In addition, this method simplifies mutagenesis.

The invention provides the URMAC method, which allows for the insertion of one or more nucleotides in a DNA targeted for nucleotide(s) insertion, substitution of one or more nucleotides in a DNA targeted for nucleotide(s) substitution, deletion of one or more nucleotides from a DNA targeted for nucleotide(s) deletion, or a combination of any insertion, substitution or deletion. The site of mutation within the Original DNA to be modified is referred to as the "Modification Target." The Modification Target may be the point of insertion or the nucleotide(s) targeted for substitution or deletion. The Modification Target is within a longer stretch of DNA, referred to as the "Target-containing DNA Fragment (TDF)" which is amplified by the PCR reactions of the method of the invention. The TDF, consisting of the Modification Target, flanking sequences, the restriction enzyme sites, and the primer hybridization sites, may be of any PCR-amplifiable size. For example, the TDF may be about 0.1 kbp, 0.5 kbp, 2 kbp, 5 kbp, 10 kbp, 20 kbp, 30 kbp, 40 kbp or 50 kbp.

The TDF is encompassed within a larger linear or circular DNA, referred to herein as the "Original DNA". The TDF, within the Original DNA, contains unique restriction sites to facilitate cleavage of the Modification Target. It is preferred that the TDF contains two unique restriction sites to facilitate replacement of the Modification Target from the Original DNA with the Linear Modified DNA, defined below, by cleavage at the restriction sites using the same unique restriction enzymes. The Original DNA sequence may be of any size and the invention particularly contemplates Original DNA sequences that are greater than five kbp.

The invention provides methods for generating any type of modification ("modification" and "mutation" are used interchangeably herein) in the Original DNA. Such modifications include insertions, deletions, and substitutions of one or more nucleotides or combinations of any of these. These modifications may generate a Linear Modified DNA, a Closed Modified DNA and/or a Modified Original DNA, all of which are defined below.

An insertion in the Original DNA is a modification in which one or more nucleotides are inserted into a location within the Original DNA molecule. Insertions of any number of nucleotides within the Original DNA are contemplated. Sequences can be inserted several ways using URMAC methods, including the incorporation of the desired insert sequence in the 5' extension of one of the oligonucleotide Opener Primers or incorporation of a part of the insert sequence in the 5' extension of one of the Opener Primers and incorporation of another part of the insert sequence in the 5' extension of the other Opener Primer, or by the incorporation of unique restriction sites in the 5' extension in one or both of the Opener Primers. Unique restriction sites inserted in this manner can be used for subsequent cloning of large DNA sequences into these sites either in the Intermediate DNA during the URMAC methods or in the Modified Original DNA following the URMAC methods.

The restriction sites used may generate sticky/cohesive-ended nucleotide sequences or blunt-ended nucleotide sequences. A sticky-ended nucleotide sequence is generated by a restriction enzyme that cuts both strands of a nucleotide sequence at different sites creating 3'- or 5'-overhangs generally of 1 to 4 nucleotides (so-called sticky or cohesive ends) or by a combination of sense and antisense DNA nicking enzymes, or by other DNA modifying enzymes such as exonucleases like exonuclease III. A blunt-ended nucleotide sequence is generated by a restriction enzyme that cuts across both strands of a nucleotide sequence at the same point creating blunt ends that do not have 3' or 5' overhangs on the cut DNA, or by DNA exonuclease enzymatic treatments that remove 3' or 5' overhangs from double stranded DNA. A blunt-ended nucleotide sequence is also generated by PCR with certain DNA polymerases such as Vent or Pfu, or by PCR with DNA polymerases such as Taq that add a non-templated adenine residue to the end of PCR product DNA, which is subsequently removed by an exonuclease.

Insertions by the URMAC methods may include the addition of open reading frames, translation start signals, translation termination signals, replication promoters, transcription promoters, transcription termination signals, enhancers, polyadenylation signals, splice donor sites, splice acceptor sites, introns, exons, codons for additional amino acid sequences, or untranslated regions including but not limited to 5' untranslated regions, 3' untranslated regions, spacers, restriction enzyme sites, siRNAs, miRNAs, a combination of any of these, and any other functional or non-functional DNA.

A deletion in the Original DNA is a modification in which a portion of the DNA is removed, lost, omitted or deleted. Deletions of any number of nucleotides of the Original DNA are contemplated. The Modification Target for deletion can be of any size between the unique restriction sites. As an example, a deletion or insertion can be designed to cause a frame-shift in an open reading frame, which may alter the encoded protein sequence.

A substitution in the Original DNA is a modification that exchanges one or more nucleotides for the same number of different nucleotides. A Modification Target to be substituted may vary in size up to the maximum capability of oligonucleotide chemical or biochemical synthesis. Such substitutions include, but are not limited to, nonconservative and conservative substitutions. Nonconservative substitutions are those that change one codon to another codon that encodes a different amino acid and result in an amino acid change in the protein encoded. Conservative substitutions are those that change one codon to another codon that encodes the same amino acid and cause no change in the protein encoded. Substitutions further include those that change an amino acid-encoding codon to a "stop" codon that causes production of a truncated protein. Substitutions may also include those codons that change a stop codon to an amino acid-encoding codon that may allow production of an elongated protein. Any combination of insertions, deletions, and/or substitutions can be simultaneously incorporated into a DNA by URMAC.

The URMAC methods may be carried out with Original DNA from any DNA sequence, including DNA made by chemical, biochemical, or biological means, DNA of synthetic origin, DNA generated from any type of RNA, or DNA derived from eukaryotic, prokaryotic, plant, fungi, yeast, bacterial, viral or any other biological sources. URMAC may be carried out on any portion, part or point of a nucleic acid molecule including protein-coding sequence, non-protein-coding sequence, regulatory sequence, silent sequence, intergenic sequence, intragenic sequence, exons, introns, functional sequence, start or stop sequences.

Manipulation and mutation of only a small section of DNA, such as the TDF, by the URMAC methods reduces the DNA sequence length exposed to PCR, thereby reducing the possibility of random mutations caused by polymerase infidelity. Furthermore, sequencing the DNA portion which is manipulated during URMAC is simpler and less expensive than sequencing the entire Original DNA that would be amplified in other mutation techniques that require copying the entire plasmid, for instance.

In the URMAC methods, mutations are generated by altering or lengthening the primers used in the second PCR step (Opener Primers). "Primers" are defined as synthetic single strand oligonucleotides that are designed and synthesized to complement the nucleotides of one strand of a DNA molecule. Primers hybridize to the complementary DNA and are used to prime synthesis of DNA from their 3' terminus by a DNA polymerase. Because insertions and substitutions by URMAC are introduced into Original DNA by one or both of the 5' tails of the Opener Primers, the number of nucleotide insertions or substitutions in a single URMAC are limited only by current oligonucleotide synthesis technologies. The primers used in the URMAC methods may be added in equal or unequal amounts to the PCR reaction. Current technologies are capable of generating oligonucleotides up to 135 nucleotides in size by direct chemical synthesis. Since 15 to 20 nucleotides of each primer must be complementary to the template for PCR, the current maximal DNA inserted by this approach would be 115-120 nucleotides for each primer, for a total of 230-240 nucleotides. Longer oligonucleotides may be generated by other biochemical methods and used to carry out URMAC.

URMAC allows the deletion of any size DNA. In the basic URMAC methods, deletion within the Modification Target is limited by the length of DNA that can be amplified by PCR to generate with current techniques and enzymes the Starter DNA. To delete any size of DNA, URMAC can be performed twice on the same Original DNA, placing the same restriction site, one that is not found elsewhere in the Original DNA, in two places in the Original DNA. The Modified Original DNA can then be cleaved with this restriction enzyme and ligated to delete the intervening DNA.

In the basic URMAC methods, the TDF size is limited only by the availability of unique restriction enzyme sites flanking the Modification Target and the current limit on the size of DNA that can be amplified by PCR. Current PCR preparations and protocols allow amplification of DNA sequences up to 50 kbp in length. Currently available thermostable DNA polymerases and their commercial preparations such as EXL DNA Polymerase (Stratagene, U.S. Pat. Nos. 4,683,202, 4,683,195 and 4,965,188), Long PCR Mix (Fermentas, U.S. Pat. Nos. 5,500,363 and 5,352,778), and DyNAzyme EXT DNA Polymerase (Finnzymes, U.S. Pat. No. 5,416,149) can amplify DNA sequences up to 50 kb, 47 kb and 40 kb, respectively.

In the event that unique restriction sites are absent in the Original DNA flanking the TDF, DNA modified by the URMAC methods can be inserted into the Original DNA by flanking the TDF with sequences that are homologous to the DNA that flanks the insertion site in the Original DNA. In this case, the Linear Modified DNA is inserted into the Original DNA by homologous recombination.

In one embodiment, the invention provides for methods of cloning double stranded DNA sequences of any size. One or more unique restriction sites are included as 5' extensions in the Opener Primers. Upon completion of URMAC steps and generating the Modified Original DNA, these restriction sites can be used to insert DNA sequences of any size.

In another embodiment, the invention provides for methods of cloning large double stranded DNA sequences. If the Original DNA is very large, it likely contains multiple sites for all available restriction enzymes and therefore no unique sites. In this case, restriction sites added in the Opener Primers can be used to insert a DNA sequence into the smaller Intermediate DNA, where unique restriction sites are more likely to be available. Completion of the URMAC methods by using homologous recombination will result in insertion of the DNA of interest into the Original DNA.

In another embodiment, DNA from one source may be modified by the URMAC methods and inserted into an Original DNA from another source to produce a Modified Original DNA.

In another embodiment, the invention provides for methods of cloning large double stranded DNA sequences using a large primer produced by PCR. In these methods, the Closed Starter DNA is contacted with a DNA polymerase and two Opener Primers, one or both of which is generated in a separate PCR reaction and can be of any size that can be amplified by PCR.

In another embodiment, URMAC is useful for modification of DNA sequences in smaller plasmids. Presently, such mutations are accomplished either by direct mutagenesis techniques such as QuickChange™ (Stratagene) or by inverted PCR. In both cases, a single base pair insertion, deletion, or replacement by these methods requires amplification of the whole plasmid. Despite the availability of high fidelity DNA polymerases, such as Pfu and Vent, the chances of introducing unwanted mutations elsewhere in the plasmid increases proportional to plasmid size. URMAC limits the region exposed to amplification and, therefore, the possibility of unwanted mutations.

Mutagenesis of some plasmids, even in the 4-8 kbp range, is not straightforward, often for unknown reasons. Furthermore, mutagenesis schemes often require trial and error. In these cases, URMAC is a practical alternative, since it relies simply on PCR, ligation, and restriction digestion. In many cases, this method will be less expensive in addition to being simpler and quicker.

The invention also provides for methods of directionally cloning of a nucleic acid sequence using the URMAC method. For directional cloning, the Target DNA fragment is amplified with one unique restriction site near each end, wherein digestion with the corresponding restriction enzymes generates sticky ends, blunt ends, or one of each. These methods include the steps of digesting the Linear Modified DNA and the Original DNA with the same restriction enzymes that cut each molecule once. The method also comprises the step of ligating the Linear Modified DNA between the restriction sites with the appropriate Original DNA fragment to directionally clone the Linear Modified DNA into the Original DNA.

In another embodiment, the inserted, mutated, deleted, amplified or cloned DNA sequence is a sequence with specific functions such as promoters or genes for the production of proteins, peptides and RNAs of all types, e.g., mRNA, ribosomal RNA, ribozymes, small inhibitory RNA, antisense RNA, double stranded regulatory RNA. DNA sequences that do not have a specific function can also be inserted, mutated, deleted, amplified or cloned. The double strand DNA to be inserted into the Original DNA can be coding or non-coding DNA molecule(s). Non-coding DNA can be used as a spacer, a gene disruptive sequence, or other non-coding DNAs such as promoters, enhancers, terminators, restriction sites, and protein binding DNA, to name a few possibilities. The DNA to be inserted can also be a combination of any two or more such elements. The DNA to be inserted can be synthetic or derived from a biological source, or a combination thereof.

In another embodiment, the invention provides for methods of modifying non-replicating DNA including covalently closed linear double stranded DNA. In one use of the URMAC technique on non-replicating DNA, a promoter can be attached to a DNA sequence by incorporating the promoter sequence in the 5' extension of a Starter Primer and the DNA can be modified by any of the methods described. This DNA can then be transfected, electroporated, or injected into target cells or an organ for expression of the encoded RNA. Such a DNA could be used for gene therapy or for insertion into the chromosome by homologous recombination. The RNA product transcribed from such a DNA could be transfected into cells to express the desired protein or it could be used to modify an RNA virus by homologous recombination.

In another embodiment, the invention provides for methods of modifying RNA directly through the use of an RNA amplifying enzyme and an RNA ligase as these technologies are advanced.

The invention also provides for kits comprising a DNA polymerase, a DNA polymerase buffer, a DNA ligase and its buffer, a control template (for example, pUC18 or other plasmid), control Starter Primers, control Opener Primers, specific restriction enzymes or any combination of these kit components and a package insert providing instructions to carry out the methods of amplifying, modifying or mutating nucleic acids using the methods of the URMAC invention. An exemplary package insert appears in FIG. 7.

The URMAC Techniques

The basic URMAC techniques involve two PCR reactions, two ligation reactions, and one restriction digestion to create DNA mutations or modifications such as insertions, deletions or substitutions. An additional optional $3^{rd}$ PCR reaction may be included to enrich for the modified target DNA. A third ligation reaction is required to insert Linear Modified DNA into the Original DNA. The method is carried out on a nucleic acid referred to as the "Original DNA" which is a large linear or circular DNA that comprises the TDF, containing the Modification Target. The Modification Target within the TDF is flanked by unique restriction sites to facilitate later replacement of this portion of the Original DNA with the mutated TDF DNA. A restriction site is a specific DNA sequence at which a restriction or nicking enzyme will cleave the DNA. Two pairs of custom-made oligonucleotides (Starter Primers and Opener Primers) are used in the PCR reactions of the methods of the invention. The steps involved in URMAC are illustrated in FIG. 1 and are described below:

PCR #1 and Ligation #1

The TDF is amplified by PCR from the linear or circular Original DNA (exemplary circular DNA depicted in the FIG. 1A) using two Starter Primers (SP1 and SP2) to produce the Starter DNA. The "Starter Primers" are oligonucleotides that anneal to segments of the Original DNA sequence in a region flanking both the Modification Target and the unique restriction sites (designated as "X" and "Y" in FIG. 1) such that the DNA synthesized by PCR includes the Modification Target site and the unique restriction sites.

The term "Starter DNA" refers to the nucleic acid resulting from the first PCR reaction of the URMAC technique. The Starter DNA is generated using the Starter Primers of the invention. The Starter DNA serves as the starting point for the introduction of the modification or mutation of interest, and the unique restriction sites (X and Y) are included in the amplified Starter DNA (FIG. 1B). These restriction sites will be used in the final step for insertion of the Modified DNA into the Original DNA (FIGS. 1F, 1G and 1H). Generally, the Starter Primers are phosphorylated at their 5' ends so that they can participate in ligation. The circularization reaction of the Starter DNA requires a phosphate group be added to the 5' end of the Starter Primers. Alternatively, an identical restriction site is included in both Starter Primers and the resulting Starter DNA is digested by the corresponding enzyme, leaving 5' phosphates. The 5' and 3' ends of both DNA strands of the Starter DNA are ligated to each other (self-ligated) to generate Closed Starter DNA (FIG. 1C). The term "Closed Starter DNA" refers to the result of the self-ligation of the Starter DNA in the first ligation step of any of the URMAC methods of the invention. Self-ligation refers to joining the two ends of a single fragment of double-stranded linear DNA to form a double-stranded circular DNA.

Preferably, the PCR reactions of URMAC are carried out with any DNA polymerase with proof-reading capacity, such as Vent or Pfu that does not add an adenosine to the 3' termini of the PCR product. A DNA polymerase that adds an adenosine to the 3' end, such as Taq DNA polymerase, may be used in URMAC provided that the 3' adenosine overhang is thereafter removed by an exonuclease. In addition, the ligation reactions of URMAC are carried out with a DNA ligase, such as T4 DNA ligase.

"Starter Primers" refer to the primers used in the first, and again in the optional third, PCR reactions (FIGS. 1A and 1E, respectively) of the methods of the invention. Generally, the Starter Primers will anneal to opposite strands within TDF of the Original DNA and direct DNA extension toward each other to copy and amplify the Modification Target and the flanking restriction sites. This allows for the Starter Primers to direct amplification of the Starter DNA and define the termini of the TDF. For example, as shown in FIG. 1A, Starter Primers, SP1 and SP2, anneal to the Original DNA, direct DNA extension toward the Modification Target and therefore will amplify the Modification Target and restriction sites X and Y. The Starter DNA from PCR#1 is self-ligated using T4 DNA ligase to generate the Closed Starter DNA.

PCR #2 and Ligation #2

The Closed Starter DNA is opened at the Modification Target using Opener Primers that are designed to contain the intended mutation proximal to or at one or both 5' ends. These primers anneal to opposite strands so that their 5' ends are proximal and their 3' ends are distal relative to each other. The Opener Primers are directed to extend DNA replication away from the point of mutation (Modification Target) in the second PCR reaction, one clockwise on one strand and the other counter-clockwise on the other strand. "Opener Primers" refer to the primers used in the second PCR reaction of the methods of the invention. The Opener Primers generate the modification in the Modification Target, and direct extension in opposite directions away from the Modification Target. There are two purposes that are accomplished simultaneously during this step. The first is to open or cut the Modification Target at a specific site to introduce the desired modification in analogous way to cutting with a restriction enzyme, but without the need for a restriction site. The second purpose is to introduce desired modifications that are incorporated into the Opener Primers. Annealing of the Opener Primers to the Closed Starter DNA allows for amplification of the entire Closed Starter DNA to generate the "Intermediate DNA" (FIG. 1D).

The term "Intermediate DNA" refers to the DNA resulting from the second PCR reaction of the methods of the invention. Intermediate DNA is linear, double stranded and contains the original unique restriction sites which are located near the center of the Intermediate DNA rather than near the termini. The Intermediate DNA termini are ligated to each other with a DNA ligase (self-ligation), such as T4 DNA ligase, to generate the "Closed Intermediate DNA". The Intermediate DNA is generated with the Opener Primers and contains the mutation of interest. "Closed Intermediate DNA" refers to a self-ligated, circular Intermediate DNA (FIG. 1E).

This step allows for insertions within the Modification Target at a specific site by adding nucleotides to the 5' terminus of one or both of the Opener Primers. This step also allows for substitutions within the Modification Target at a specific site by changing one or more nucleotides in one or both Opener Primers. This step also allows for deletions within the Modification Target at a specific site by moving the Opener Primers apart. Annealing of the Opener Primers to nonadjacent segments of the Closed Intermediate DNA outside the Modification Target, as described, results in only a portion of the TDF DNA being amplified, effectively deleting the portion of the TDF that is not amplified. The deletion is accomplished by having the Opener Primers anneal to the Closed Starter DNA at positions that are separated by intervening nucleotides adjacent to, but outside of the Modification Target that is to be deleted. The portion of sequence between the 5' ends of the Opener Primers is omitted from the amplified DNA.

A combination of insertions, deletions, and/or mutations can be simultaneously incorporated into a DNA by the Opener Primers used in the URMAC methodologies. Thus, the term "adjacent" refers to nearest in space or position or immediately adjoining without intervening nucleotides. Annealing of the Opener Primers to nonadjacent segments of the Intermediate DNA allows for deletion of a portion of the Intermediate DNA. The term "nonadjacent" refers to not immediately adjoining or having at least one intervening nucleotide. An Opener Primer containing mutation(s) may need to be lengthened to assure efficient annealing if insertion or substitutions are included in the primer.

PCR #3 (Optional) and Ligation #3

As an optional enrichment step for the Closed Intermediate DNA, the Closed Intermediate DNA is amplified by the Starter Primers that were used to amplify the Starter DNA in the first PCR step (SP1 and SP2 in FIG. 1A). This PCR step (FIG. 1E) generates the "Linear Modified DNA" (FIG. 1F). Either the Linear Modified DNA, or the Closed Intermediate DNA, is digested (FIG. 1F) with the unique restrictions enzymes, X and Y, identified in the first step. The Original DNA is also digested with the same enzymes. The appropriate fragments may be isolated by agarose or polyacrylamide gel electrophoresis and purified. The proper fragment from the restriction enzyme-digested Linear Modified DNA or Closed Intermediate DNA is ligated to the similarly digested Original DNA (FIG. 1G) to produce a DNA with the designed mutation. The resulting DNA is termed the "Modified Original DNA" (FIG. 1H). Purification of the DNA products of the various PCR and/or ligation reactions may increase the efficiency of URMAC. Dephosphorylation of the digested Original DNA may be required to prevent self-circularization of digested Original DNA in cases of incomplete digestion, blunt end digestion or same enzyme digestion for the X and Y sites shown on FIG. 1.

The methods of the invention also contemplate repeating the steps of PCR #2 and Ligation #2 using different Opener Primers to generate one or more additional modification insertions, substitutions or deletions, or any combination thereof, in one Modification Target region.

Variations of URMAC

In a variation of URMAC, the Original DNA may contain two unique restriction enzyme sites flanking the Modification Target, one whose digestion results in a blunt end and the other whose digestion results in a sticky end. In that case, one Starter Primer is positioned such that the end of the PCR product it generates can be blunt-end ligated, during Ligation #3, to the blunt end left by digestion of the Original DNA with the blunt end-producing restriction enzyme. PCR with DNA polymerases such as Vent and Pfu result in DNA with blunt ends, and the additional adenosine nucleotide added by other DNA polymerases, such as Taq, can be removed by treatment with Pfu or Vent or by an exonuclease to generate a blunt end. Digestion of the Original DNA at the second unique restriction enzyme site that flanks the Modification Target and digestion of the Linear Modified DNA at the same site will generate the same sticky end in each molecule, as described in the general description of URMAC, thereby allowing directional cloning in the third ligation step (Ligation #3).

In a variation of URMAC, the natural generation of blunt ends by many polymerases used in PCR is exploited. A DNA to be cloned is amplified by PCR and ligated to the blunt-ended Intermediate DNA, without the need for restriction digestion (FIG. 2). The polymerase used to generate both PCR products is Pfu, Vent, or most other thermostable DNA polymerases that produce blunt ends. If a DNA polymerase such as such as Taq is used to generate that PCR product DNA, the additional adenosine nucleotide added by Taq can be removed by treatment with Pfu or Vent or by an exonuclease, to generate a blunt end. Alternatively, a DNA fragment generated by digestion with restriction enzymes that result in blunt ends, or any other DNA molecule with blunt ends can be inserted to generate Closed Intermediate DNA. Molecules with the correct orientation of the insert can be selected by PCR with two of the original primers that will be adjacent in the correctly oriented molecule, one that was used to amplify the Intermediate DNA and the other that was used to amplify the DNA Insert. Together these primers will only amplify the Intermediate DNA with the correct insert orientation. After the URMAC methods are completed the DNA Insert will be in the correct orientation in the Modified Original DNA. Alternatively, rather than selecting the correct DNA Insert orientation in the Closed Intermediate DNA by PCR as shown in FIG. 2, URMAC can be completed and a clone of the Modified Original DNA with the correct orientation can be identified. The correct orientation of the DNA Insert may be determined by methods standard in the art such as digestion with restriction enzymes or PCR with selected primers that only produce a PCR product if the DNA Insert is in the correct orientation.

In a variation of URMAC, the Original DNA may contain a restriction site for the same restriction enzyme on both sides of the Modification Target, rather than two unique restriction sites. Thus, only a single restriction enzyme is used in steps where URMAC methods require restriction enzyme cleavage. The URMAC methods would be completed, but after the third ligation step (Ligation #3), a clone with the insert in the correct orientation would be selected as the correct Modified Original DNA.

In another variation of URMAC, the Original DNA may contain two sites for a particular blunt end cutting restriction enzyme that flank the Modification Target. Upon completion of the URMAC methods, a clone with the insert in the correct orientation would be selected as the correct Modified Original DNA.

In another variation of URMAC, one or two unique restriction sites that are not found in the Original DNA, are incorporated into the Opener Primers and the URMAC methods are completed to generate a Modified Original DNA containing this or these unique restriction sites. A DNA of any size is inserted into this or these sites by restriction digestion, purification of the proper DNA fragments and ligation.

In a further variation of URMAC, a DNA sequence of any size is inserted into the Intermediate DNA by restriction digestion and ligation (FIG. 3). Since the Intermediate DNA is small compared to the Original DNA, a much wider variety of unique restriction sites will be available for inclusion than would be available in the Original DNA. These unique sites can be used to insert any DNA sequence into the Intermediate DNA. In this variation, unique restriction sites are added to the Opener Primers that are used to produce Intermediate DNA in the second PCR step (PCR #2 of URMAC). The DNA Insert is amplified by PCR with primers that include these same two unique restriction enzyme sites, unless those sites are already present at the termini of the DNA of interest in which case they would not need to be added. Both the Intermediate DNA and the DNA Insert are digested with the two restriction enzymes, purified by agarose gel electrophoresis and extraction or other methods, and ligated. Any combination of sticky end or blunt end ligations can be used as described above. The resulting new Closed Intermediate DNA, with its insert, can be used to complete the URMAC methods.

In another variation of URMAC, a DNA of any size that can be amplified by PCR is inserted into the Intermediate DNA (FIG. 4). The DNA Insert is amplified by PCR with two primers, one of which (P1) contains a 5' extension that is complementary to the Target DNA in the Closed Starter DNA. P1 may be added to this PCR reaction in smaller amounts than the second primer (P2), resulting in an imbalanced PCR that produces more of the strand containing P2 than the strand containing P1. This strand is paired with a third primer (P3) to amplify the Closed Starter DNA, producing Intermediate DNA. This Intermediate DNA may be further enriched by PCR with P2 and P3, but this is optional. The Intermediate DNA that now contains the DNA Insert is self-ligated and the URMAC method is continued, as shown in FIG. 1.

In a further variation of URMAC, the method may be performed without the need for restriction sites. This capability is important in very large DNAs, since the likelihood of finding unique restriction sites becomes small as the DNA size increases. For example, a segment of the vaccinia virus genome could be amplified and mutated by URMAC, as described above, with flanking DNA but without the unique restriction sites. The mutated DNA can be transfected into mammalian cells infected with vaccinia virus. As the vaccinia virus genome replicates, it naturally recombines with DNA containing homologous regions (Blasco & Moss *J. Virol.* 65:5910-5920, 1995), such as those flanking the Modification Target in the Linear Modified DNA. The DNA of many other viruses, including the herpesviruses, most bacteria, many other microorganisms, as well as eukaryotic cells are also able to recombine within regions of homology allowing a mutant DNA sequence to be incorporated.

In a variation of URMAC, insertion of an altered DNA by homologous recombination and without the use of restriction enzymes can be made more efficient when a specialized recombinase, such as a recombinase from a bacteriophage, is included in the bacterium. This may be carried out with the method known as "recombineering" (Warming et al. *Nucleic Acids Res.* 33(4):1-12, 2006). Recombineering enables efficient insertion or deletion of DNA at any site on a plasmid of any size, without the need for restriction sites. For instance, within the bacterium a cloned herpesvirus genome that is inserted into a bacterial artificial chromosome can recombine with a mutated segment of DNA containing segments at each end that are homologous to the viral genome (Borst et al. *J. Virol.* 73:8320-8329, 1999; Tanaka et al. *J. Virol.* 77:1382-1391, 2003). The Linear Modified DNA generated by URMAC has such terminal homologous regions and so could be readily used in this system in the final step of URMAC to create Modified Original DNA (FIG. 1H). Because unique restriction sites are not required in these methods, the size of the Original DNA is no longer a limit on the size of DNA that can accept a mutation generated by URMAC.

The URMAC methods may also be used to make mutations in non-replicating DNAs. For most applications in molecular biology, the Original DNA is a plasmid that contains bacterial origin of replication, a drug resistance gene and other DNA elements that allow multiplication of the plasmid when transformed into bacterial cells. However, performing URMAC does not require an origin of replication or any other element necessary for DNA replication. A non-replicating gene expression DNA cassette that contains a promoter of interest with required elements to make the gene functional such as polyadenylation signal, and a gene of interest can be generated and modified by URMAC for use in gene therapy. This variation may include the generation of covalently closed linear DNA. For example, the cassette may be injected or transfected as a naked or protected DNA directly into cells or an organ of interest to express an RNA or a protein that performs a specific function. If a promoter for a DNA dependent RNA polymerase such as RNA polymerase I, II, or III is included in the final product, RNA can be produced from the DNA in the nucleus of cells or organs that take up the DNA. URMAC could also be used to modify non-replicating DNA molecules that can be used for homologous recombination with chromosomal DNA. URMAC could also be used, for example, to insert the replication sequences in otherwise non-replicating DNA such as PCR products.

In a further variation of URMAC, the method may be performed omitting the first URMAC ligation (Ligation #1 in FIG. 1). The addition of complementary sequences of 10-20 or more nucleotides as 5' extensions to the two Starter Primers allows the first PCR products to anneal by their complementary ends. The Starter Primers containing these extensions are referred to herein as "Oligo Instead of Ligation" primers ("OIL Starter Primers"). The 5' extensions to the OIL Starter Primers must be complementary to each other, and the complement of each OIL extension must be able to function as a good PCR primer. The reason is that during PCR the DNA strand complementary to each Starter Primer contains the complement of the Starter Primer at its 3' terminus (FIG. 8). These strands anneal to each other via their complementary OIL sequences and are extended by the polymerase to generate the full-length PCR product. This process of joining the two initial PCR products occurs without ligation. The resulting Intermediate DNA is then self-ligated to produce Closed Intermediate DNA and the basic URMAC is continued as shown in FIG. 1. In the final PCR step of the method the OIL Starter Primers can be used with or without the 5' extensions.

OIL extensions can be one of many pairs of complementary sequences. The same OIL sequences can be added as 5' extensions to any pair of Starter Primers to avoid the first ligation, as long as their sequence does not interfere with the priming activity of the 3' end of the Starter Primers through detrimental complementarity. If they do, a different OIL extension sequence can be chosen. In this URMAC variation, Opener Primers A and B do not serve to "open" the DNA template because their template is already linear. Since they do not participate in any ligation reaction, these OIL primers do not need to be phosphorylated. The number of thermocycles may be significantly reduced for the first URMAC PCR, from 20-30 cycles to as few as 10 cycles or less thereby increasing the speed and accuracy of URMAC.

It is possible to perform the reactions with these OIL primers in at least three different ways:

1) All-in-one reaction. All four primers are combined with Original DNA and PCR is performed using more of the Opener Primers than OIL Starter Primers, for example 100:1. The amount of OIL Starter Primer is kept low to avoid producing a large number of copies of the Starter DNA sequence which, in the final step of URMAC, is inserted into the Original DNA in the same manner as the Linear Modified DNA. The combination of these PCR reactions will generate the Intermediate DNA.

2) Two step reaction. A small amount of Starter DNA is generated in a PCR reaction using a small amount of OIL Starter Primer A and OIL Starter Primer B primers, for example 1 to 10 picomoles per 25 µl reaction, for a low number of PCR thermocycles, for example 5 to 15 cycles. Opener Primer A and Opener Primer B are then added to this reaction at a higher concentration, for example 100 picomoles. PCR thermocycling is continued for an additional 20-30 cycles to generate the Intermediate DNA.

3) Three step reaction. PCR1a and PCR1b are performed in two separate PCR reactions using equimolar quantities of OIL Starter Primer A and Opener Primer B in one reaction, and of OIL Starter Primer B and Opener Primer A in the other reaction. For the third PCR reaction, small quantities of the products from the first two reactions, for example 1-5 µl, from PCR1a and from PCR1b are mixed with both Opener Primers. This reaction will generate the Intermediate DNA. Alternatively, products from the first two reactions can be mixed and any DNA polymerase can be used to extend the DNA, filling in to the end to complete both DNA strands to produce Intermediate DNA, without the addition of the OP primers.

The URMAC methods may be used to modify any RNA, through a DNA intermediate. For example, an RNA could be copied into DNA by reverse transcriptase followed by PCR (RT-PCR), including the promoter for a DNA-dependent RNA polymerase, such as the T7 promoter, in one of the PCR primers. In this case, the primers are analogous to the two Starter Primers. Following mutagenesis of the DNA by one of the URMAC methods described above, the mutant DNA, either the Linear Modified DNA or the Modified Original DNA can be transcribed in vitro by the RNA polymerase corresponding to the added promoter, for example, T7 polymerase. The resulting "Modified RNA" can be transfected into cells, such as cultured animal cell, animal tissues or intact non-human animals, where it will function. If the target RNA is an mRNA, a cap can be enzymatically added before transfection to enhance its translation. If the T7 promoter is used, the DNA can instead be transfected into cells along with either the T7 polymerase protein or a gene expressing the T7 polymerase, for expression of the mutated DNA within the cell. Alternatively, the Linear Modified DNA or the Modified Original DNA can be transfected into a cell line expressing T7 RNA polymerase, where the Modified RNA would be produced. A promoter for another RNA polymerase can be used instead of the T7 promoter. For instance, a promoter for a cellular RNA polymerase I, II or III can be incorporated into the Linear Modified DNA or Modified Original DNA, and the DNA transfected into cells, such as cultured animal cells, organs or intact non-human animals where the corresponding polymerase would produce RNA. Thus, the Modified RNA can be transcribed in cultured animal cells, animal tissues or intact non-human animals transfected with the Linear Modified DNA. In addition, the modified RNA can be transcribed in vitro such as in a test tube. As another example, the original RNA could be a portion of a coronavirus genome. Following RT-PCR, URMAC, and RNA polymerase production of the mutated RNA, this RNA can be transfected into cells that are infected with the same coronavirus. Coronaviruses readily recombine with homologous RNA (Lai et al., *J Virol.* 56: 449-456, 1985; van der Most et al., *Nucleic Acids Res.* 20: 3375-3381, 1992; Phillips et al. *J. Virol.* 73:7752-7760, 1999), thereby inserting the mutation into the virus genome.

It will be possible to use these methods to mutate RNA directly, once the methods known in the art to amplify RNA are improved. RNA ligases are presently available (Silber, et al. *Proc. Natl. Acad. Sci. USA* 69, 3009, 1972; Uhlenbeck & Gumport. (1982) In: *The Enzymes*, Vol. XV Part B, Boyer, P. D. ed., Academic Press, New York, 31, 1982). For example, a mutant RNA may be produced using an URMAC method describe herein with an RNA amplifying polymerase and an RNA ligase. For example, the mutant RNA may be transfected into cells where it would function. If the RNA is an mRNA, it could be enzymatically capped before transfection to enhance its expression. As another example, a coronavirus RNA may be mutated using the URMAC method. The mutant RNA is then transfected into a cell that is infected with that coronavirus either before or after RNA transfection. Coronaviruses recombine efficiently with homologous RNA (Lai et al., *J Virol.* 56(2): 449-456, 1985; van der Most et al., *Nucleic Acids Res.* 20(13): 3375-3381, 1992), in this case resulting in a mutant virus.

Polymerase Chain Reaction

URMAC comprises steps of carrying out the polymerase chain reaction (PCR) to modify the Original DNA. As used herein, "polymerase chain reaction" or "PCR" means a process such as described in U.S. Pat. No. 4,683,195 and U.S. Pat. No. 4,683,202 for the amplification of a segment of DNA using at least two primers and a DNA polymerase. In URMAC, such a polymerase would be a thermostable enzyme. Preferably, the polymerase would be a high fidelity enzyme that has a proof-reading function to reduce the chances of introducing unwanted random errors in the product DNA.

In the methods of the invention, PCR may be carried out using a "PCR reaction mixture" which is a mixture suitable for carrying out PCR. The PCR reaction mixture will contain a suitable amount of a thermostable DNA polymerase, a linear or circular template DNA, preferably double-stranded DNA, to be amplified, a pair of oligonucleotide primers such that one of the primers is configured for annealing to one strand of the template and the other primer is configured for annealing to the other or complementary strand of the template, ATP, suitable amounts of each of the four deoxyribonucleoside triphosphates (dNTPs), and buffers, salts, preservatives, reducing agents, and water as may be required.

PCR is generally carried out by repeated cycling of the reaction mixture between temperature conditions suitable for melting or denaturation of double-stranded template DNA (usually about 95° C.), annealing of primers to the melted (i.e. single-stranded) template DNA (usually about 50° C.), and elongating the annealed primers by primer extension (usually about 68° C. to about 72° C.). The thermostable DNA polymerases typically used in PCR survive these cycles of temperature change.

The PCR steps of the methods of the invention will be carried out at temperatures suitable for denaturing the template, which are temperatures at which the template is melted or denatured in view of the conditions present in the reaction mixture that are known to affect melting of nucleic acids, such as strandedness, monovalent cation concentration, GC content, length of the nucleic acid, presence or absence of mismatches, and concentration of certain solvents that affect melting. These factors are well known in the art, as are empirical formulas for determining thermal melting temperatures under selected conditions. A temperature above the thermal melting temperature ($T_m$) of the template will be selected. Denaturation temperatures of about 95° C. are typical.

Further, the PCR steps of the methods of the invention will be carried out at temperatures suitable for annealing the primers to the denatured template, which are temperatures at which the single-stranded primers will anneal to the denatured (single-stranded) template nucleic acid. The same factors that affect denaturation also affect annealing. Since the hybridizing portion (the 3' termini) of the primers are typically in the range of about 10-30 nucleotide residues in length as opposed to templates that are usually thousands of nucleotide residues in length, and since thermal melting temperatures of short nucleic acids are lower than for longer nucleic acids, the annealing temperature will be well below the thermal melting temperature of the template. An annealing temperature of about 40-55° C. is typical.

Primers of the invention are oligonucleotides that are paired with one or the other strand of DNA and provide a free 3'-OH at which a DNA polymerase starts synthesis of a DNA chain. The primers direct amplification of the target nucleic acid during PCR reactions. For a PCR reaction, oligonucleotide primers anneal to DNA strand complementary to their sequence flanking the region of interest in the target DNA. The primers used in the methods of the invention may be phosphorylated at the 5' end to allow the primers to participate in the ligation reaction. The Opener Primers of the invention that are designed to create nucleotide insertion mutations or nucleotide substitution mutations may contain the desired mutations at their 5' tail on one or both primers.

The term "annealing" refers to the pairing of complementary DNA or RNA sequences, via hydrogen bonding, to form a double-stranded molecule. This term refers to the hybridizing or binding of the primers to the template target DNA during the PCR reaction. The annealing temperature in a PCR reaction depends directly on length and composition of the primers. Generally, the annealing temperature (Ta) should be about 5° C. below the lowest Tm of the primer pair. The process of primer annealing is less than one minute; and most primers will anneal efficiently in 30 seconds or less, unless the Ta is too close to the Tm, or unless the sequences are unusually long. Optimal annealing temperatures of the primers and primer concentrations must be determined empirically. Primers are always present at an excess of template and equal concentration in conventional (symmetric) PCR amplification and, typically, are within the range of 0.1 µM to 1 µM.

The length of the annealing portion of a primer depends upon its (A+T) content, and the Tm of its partner. In addition, the primer should be complex enough to decrease the likelihood of the primer annealing to sequences other than the chosen target. The methods of the invention may utilize primers ranging in length from 10-30 nucleotides, preferably the primers will be 17 nucleotides in length except for the Opener Primers that introduce insertion or substitution mutations. These Opener Primers contain a 10 to 30 annealing head at their 3' ends and all the desired mutations at their 5' tails and their length depends on the amount of desired mutations. Generally, a 40%-60% G+C content is recommended for the annealing portion of primers, avoiding internal secondary structure and long stretches of any one base except at the 5' tails of the Opener Primers that may contain the desired mutations. In addition, primers should not anneal to regions of secondary structure (within the target) having a higher melting point than the primer. Non-template, complementary 5' extensions may be added to primers to allow a variety of useful post-amplification manipulations of the PCR product without significant effect on the amplification itself. These 5' extensions may be any DNA sequence such as restriction sites, promoter sequences, or sequences for insertion or substitution within the target sequence.

The length of the primers used in URMAC will be dependent on the state of the art for oligonucleotide synthesis. It is expected that there will be advances in the oligonucleotide synthesis technologies, which may allow for the synthesis of primers larger than 135 nucleotides long. The size of insertion mutations generated by the URMAC technique will depend of the size of the Opener Primers and therefore depend on oligonucleotide synthesis capabilities in the art.

The methods of the invention may be carried out with a high fidelity polymerase. High fidelity DNA polymerase refers to any DNA polymerase or polymerases mixture that has a reduced rate of spontaneous polymerization errors and contains a proof reading function. For the purposes of these methods, the polymerase also does not add adenosine nucleotide at the 3' end of DNA. High fidelity polymerases may be specially designed for highly accurate and efficient amplification of large DNA fragments. High fidelity polymerase also may be a combination of thermostable polymerase enzyme and thermostable polymerase activity-enhancing molecules. High fidelity polymerases have the ability to amplify GC-rich or other difficult templates. High-fidelity enzymes generally have a 3'→5' (editing) exonuclease activity to remove incorrectly incorporated bases. This exonuclease activity reduces the mutations per base pair per cycle from about $10^{-4}$ to about $10^{-5}$.

The methods of the invention may be carried out with any high fidelity DNA polymerase including Vent, also known as Tli (*Thermococcus litoralis*), Pfu (*Pyrococcus furiosus*), UlTma (*Thermotogo maritime*) or Pwo (*Pyrococcus woesei*). Any of the methods of the invention may comprise a commercially available high fidelity DNA polymerases such as PfuUltra (Stratagene, LaJolla, Calif.), Pwo Superyield (Roche, Indianapolis, Ind.), Platinum Pfx (Invitrogen, Carlsbad, Calif.), VentR (New England Biolabs, Ipswich, Mass.), DeepVentR (New England Biolabs), UlTma (Invitrogen), Accuprime Pfx (Invitrogen), Phusion (Finnzyme, Espoo, Finland), Platinum Taq (Invitrogen), FideliTaq (USB, Cleveland, Ohio) or Hot Start HiFidelity (Qiagen, Valencia, Calif.).

PCR steps of the methods of the invention will be carried out at temperatures suitable for polymerase-catalyzed extension of the primers, which are temperatures at which the thermostable DNA polymerase is active. Preferably, the temperature is near the temperature optimum of the enzyme. For example, the Vent DNA polymerase is maximally active at about 72-75° C. and remains functional at 86° C. (Kong et al., *Proc. Natl. Acad. Sci. USA* 268: 1965-1975, 1996). Pfu polymerase is maximally active at about 72-74° C. and remains functional at 95° C. (Lundberg et al., *Gene* 108: 1-6, 1991). This is typical of thermostable polymerases.

Deoxyribonucleoside triphosphates include 2'-deoxyadenosine 5'-triphosphate (dATP), 2'-deoxycytidine 5'-triphosphate (dCTP), 2'-deoxyguanosine 5'-triphosphate (dGTP), and 2'-deoxythymidine 5'-triphosphate (dTTP). Generally, the concentration of dNTP in the PCR reaction is about 200 µM. It is important to keep the four dNTP concentrations above the estimated $K_m$ of each dNTP (10 µM-15 µM) and balanced for best base incorporation. Lowering the concentrations of dNTP and magnesium ion by an equal molar concentration can improve fidelity. Modified dNTPs (dig-11-dUTP, 5-bromo-dUTP, inosine, biotin-11-dUTP, biotin-16-dUTP and 7-deaza dGTP) and 2'-deoxyuridine 5'-triphosphate (dUTP) also may be used.

Exemplary PCR buffers contain a salt such $MgCl_2$. The $MgCl_2$ is added as a cofactor for the DNA polymerase. Additional co-solvents may also be added, such as formamide, glycerol or DMSO. These co-solvents are useful for amplifying G+C-rich target nucleic acids or through regions of strong secondary structure.

Ligation

Ligation is an enzymatic reaction resulting in the formation of a phosphodiester bond between the 5' phosphate of one strand of DNA and the 3' hydroxyl of another. DNA ligases are enzymes used to covalently link or ligate fragments of DNA together. The ligation reactions should be carried out at a temperature that balances the melting temperature $T_m$ of the DNA overhangs (sticky ends) that may be generated by restriction enzymes. If the ambient temperature exceeds $T_m$, homologous pairing of the sticky ends will not occur because the high temperature disrupts the weak hydrogen bonding. The shorter the DNA overhangs, the lower the $T_m$. Since the overhangs are usually 4 to 6 nucleotides long, ligation experiments are usually performed at low temperatures ranging between 4 and 20° C. and typically at 12° C. Blunt end ligations are also performed at low temperatures but the amount of DNA ligase and/or the reaction incubation time is extended. DNA ligation however, can be performed in a short incubation time in certain buffers For example, T4 ligase will ligate DNA fragments with complementary sticky ends or blunt ends at 37° C. for 20 minutes in exemplary ligation buffer (60 mM Tris-HCl, pH 7.5, 60 mM $MgCl_2$, 50 mM NaCl, 1 mg/ml BSA, 70 mM β-mercaptoethanol, 1 mM ATP, 20 mM dithiothreitol, 10 mM spermidine).

The methods of the invention may be carried out with any DNA ligase. These DNA ligases include ATP-dependent DNA ligases such as T4 DNA ligase, the preferred ligase to carry out the ligation steps in the methods of the invention, and T7 DNA ligase, and NAD-dependent DNA ligases such as *E. coli* DNA ligase and *B. stearothermophilus* DNA ligase. The methods of the invention may also be carried out with thermostable DNA ligases such as Taq (*Thermus aquaticus*) DNA ligase, Pfu (*Pyrococcus furiosus*) DNA ligase and Tfi DNA ligase. Thermostable DNA ligases include any DNA ligase that maintains its activity for ligating DNA after being exposed to a multiple cycles of thermocycling as would occur in PCR. Although thermostable ligases do not ligate blunt DNA, such reactions can be performed in the presence of additional "helper" oligonucleotides that hybridize the 5' end of one DNA strand to the 3' end of another DNA strand of the same polarity such that the two DNA single strands form a temporary nick with the helper oligonucleotide. That nick may be closed by thermoligases. The other DNA strands are also ligated in a similar fashion. Because thermoligases are not very efficient, the process of thermoligation must be carried out in a thermocycler for several cycles.

For example, Pfu DNA ligase is highly thermostable, having a half-life of greater than 60 minutes at 95° C. The optimum temperature for nick-sealing reactions is about 70° C. with this enzyme. Further, Taq DNA ligase catalyzes the formation of a phosphodiester bond between juxtaposed 5'-phosphate and 3'-hydroxyl termini of two adjacent oligonucleotides that are hybridized to a complementary DNA. Taq DNA ligase is active at elevated temperatures (45° C. to 65° C.) (Barany, *Proc. Nat'l Acad. Sci. USA* 88:189, 1991, Takahashi et al., *J. Biol. Chem* 259:10041-10047, 1984). In addition, AMPLIGASE thermostable DNA ligase (Epicentre Technologies) catalyzes the NAD-dependent ligation of adjacent 5'-phosphorylated and 3'-hydroxylated termini in duplex DNA structures. This enzyme has a half-life of 48 hours at 65° C. and greater than 1 hour at 95° C. This thermostable DNA ligase has also been shown to be active for at least 500 thermal cycles (94° C./80° C.) or 16 hours of cycling (Schalling et al., *Nature Genetics* 4:135, 1993).

Steps of the methods of the invention will be carried out at temperatures suitable for ligase-catalyzed closing of the extended primers meaning a temperature at which the DNA ligase is active. Preferably, this temperature is near the optimum temperature of the enzyme and can be the same temperature selected for carrying out the polymerase-catalyzed extension reaction.

It will be recognized that many enzymes of the invention including polymerases and ligases require cofactors for activity. For example, T4 DNA ligase requires ATP as a cofactor. Therefore, a reaction catalyzed by T4 DNA ligase will require an appropriate amount of ATP being added to the reaction mixture.

BRIEF DESCRIPTION OF DRAWING

FIG. 1A depicts a circular Original DNA, such as a plasmid, the location of the Modification Target within the TDF, the flanking unique restriction sites (X and Y) and the sites where the Starter Primers (SP1 and SP2) anneal. X and Y refer to the unique restriction sites within the Original DNA and the TDF copied from the Original DNA by PCR #1. FIG. 1B depicts the linear Starter DNA generated by PCR #1. FIG. 1C depicts the Closed Starter DNA generated by Ligation #1 and the location on the Closed Starter DNA, close to or within the Modification Target, on which the Opener Primers (OP1 and OP2) hybridize. In this example, OP1 contains a sequence to be inserted as a 5' extension of the primer (stippled line). FIG. 1D depicts the Linear Intermediate DNA generated by PCR #2, using primers OP1 and OP2. FIG. 1E depicts the Closed Intermediate DNA generated by Ligation #2 and the location where primers SP1 and SP2 anneal to the Closed Intermediate DNA. FIG. 1F depicts the Linear Modified DNA generated by PCR #3, using primers SP1 and SP2, and the restriction enzyme digestion of the Linear Modified DNA. FIGS. 1G and 1H depict the final steps of inserting the restriction digested Linear Modified DNA into the Original DNA that is digested with the same restriction enzymes, to generate the Modified Original DNA, such as a plasmid, by ligation.

FIG. 7 depicts the results of the three PCR reactions involved in the basic URMAC methods followed by verification of successful execution of URMAC procedures. FIG. 7A, upper panel, depicts agarose gel electrophoretic analysis of the first PCR product (Starter DNA); the middle panel depicts the PCR products (Intermediate DNA) for insertion (I) of an Mlu I restriction site into the pUC18 plasmid, substitution (S) of the Nde I restriction site with an Mlu I site, and deletion (D) of the native Nde I site from the same plasmid; the lower panel depicts the final PCR product (Linear Modified DNA) for all three mutations.

FIG. 8 depicts a variation of the URMAC protocol that modifies the Starter Primers, thus rendering the first URMAC ligation unnecessary. This modification is referred to as "Oligo instead of Ligation" (OIL). The Original DNA is mixed with OIL Starter Primers (SP) A and B and Opener Primers (OP) A and B. OIL SPA and OIL SPB each have two functional regions: a 3' sequence complementary to the Original DNA and a 5' OIL sequence that is complementary to the 5' OIL extension on the other SP. The 5' OIL sequences from Example 3 are shown in the open boxes. The PCR-generated complement of these 5' OIL sequences are indicated with italics. These complementary sequences, themselves, serve as primers in the PCR1c reaction. OPA and OPB contain the desired mutation. In the case shown here the mutation is an insertion represented by the 5' extension on OPB. Two PCR reactions, PCR1a and PCR1b, each produce PCR products. The two strands that contain the complement of the OIL sequence at their 3' ends, one strand from each PCR product, anneal and extend in the PCR1c reaction, generating the Intermediate DNA. The Intermediate DNA is then self-ligated and the method is completed as described for the basic URMAC in FIG. 1. Details of the OIL modification to URMAC are found in Example 3 below.

DETAILED DESCRIPTION OF THE INVENTION

The following examples illustrate the invention. The first example describes the deletion of the M1, the M2, and both the M1 and M2 open reading frames of the human respiratory syncytial virus from a modified full-length cDNA clone using the URMAC methods. Additionally described in Example 2 are URMAC reactions that result in nucleotide insertion, substitution, or deletion in a Modification Target. Example 3 describes an URMAC variation in which the Starter Primers are OIL primers allowing elimination of the first URMAC ligation.

EXAMPLE 1

Deletion of Two Open Reading Frames from a Large Plasmid Using URMAC

Human respiratory syncytial virus (RSV) is a negative strand RNA virus for which a complete genomic cDNA clone has been assembled and inserted into the plasmid pBR322 (Collins et al. *Proc Natl Acad Sci USA* 92(25): 11563-7, 1995). The RSV cDNA can be manipulated to add, delete, or mutate genes. Infectious RSV can then be "rescued" from this genomic cDNA as a self-replicating RNA virus in cultured cells. To accomplish this rescue, cells were transfected with the genomic plasmid and 4 other plasmids that produce the 4 RSV proteins needed for RSV replication. T7 polymerase provided by another virus or plasmid drives transcription of the RSV genomic RNA and of the mRNA for the 4 RSV proteins. Once translated, these 4 proteins support the initial rounds of RSV replication, after which the virus produces its own mRNA and proteins (Collins et a., supra.; Techaarpornkul et al., *J Virol,* 75:6825-34, 2001).

A modified version of the RSV cDNA in pBR322 was used in this study. The 17 kbp plasmid contained a modified cDNA in which the RSV attachment and fusion glycoprotein genes were removed and a blasticidin gene inserted in their place for selection purposes, and a green fluorescent protein gene was inserted upstream of the first viral gene for detection purposes. The resulting genome was rescued as a "replicon" that is able to replicate as RSV in cells but not able to assemble infectious particles or spread to other cells.

The URMAC methods were used to individually, and collectively, delete the M2-1 and M2-2 open reading frames (ORFs) from one RSV gene. These two ORFs overlap each other within the M2 gene and both proteins produced from these ORFs play integral roles in RSV replication. M2-1 is a transcription anti-terminator, required to transcribe full-length mRNA from the RSV genes (Collins et al. *Proc Natl Acad Sci USA* 93(1): 81-5, 1996). M2-2 controls the balance between mRNA transcription and genome replication (Bermingham et al., *Proc Natl Acad Sci USA*

TABLE 1

Primers Used in URMAC to Delete the M2-1, M2-2, and Both M2 Open Reading Frames from the Replicon plasmid MP312

| Primer | Sequence | SEQ ID NO: |
|---|---|---|
| SP1* | 5' P-ACTTGTATCGTCGCCATCGG | 1 |
| SP2 | 5' P-AGAAACGTAGTCCTGATAAC | 2 |
| OP1** | 5' P-ATTTGCCCCAGTTTTCATTTTTAC | 3 |
| OP2 | 5' P-CAAATGACCATGCCAAAAATAATGATAC | 4 |
| OP3 | 5' P-GTCAGGTAGTATCATTATTTTG | 5 |
| OP4 | 5' P-CACCACATCGTTACATTATTAATTC | 6 |

96(20): 11259-64, 1999).

Neither inverted mutagenic PCR (Byrappa et al., *Genome Res* 5(4), 404-7, 1995) nor the QuickChange™ (Stratagene) method could be used to generate these deletions because the plasmid is too large to be copied efficiently by PCR in vitro. There are no unique restriction sites within or near the M2 gene region, ruling out the replacement of the M2 gene with a synthetic oligonucleotide. Furthermore, precision is required in removing one ORF without affecting the other, ruling out deletion by restriction enzyme digestion, fill-in or trimming reactions, and ligation.

Figure 5:
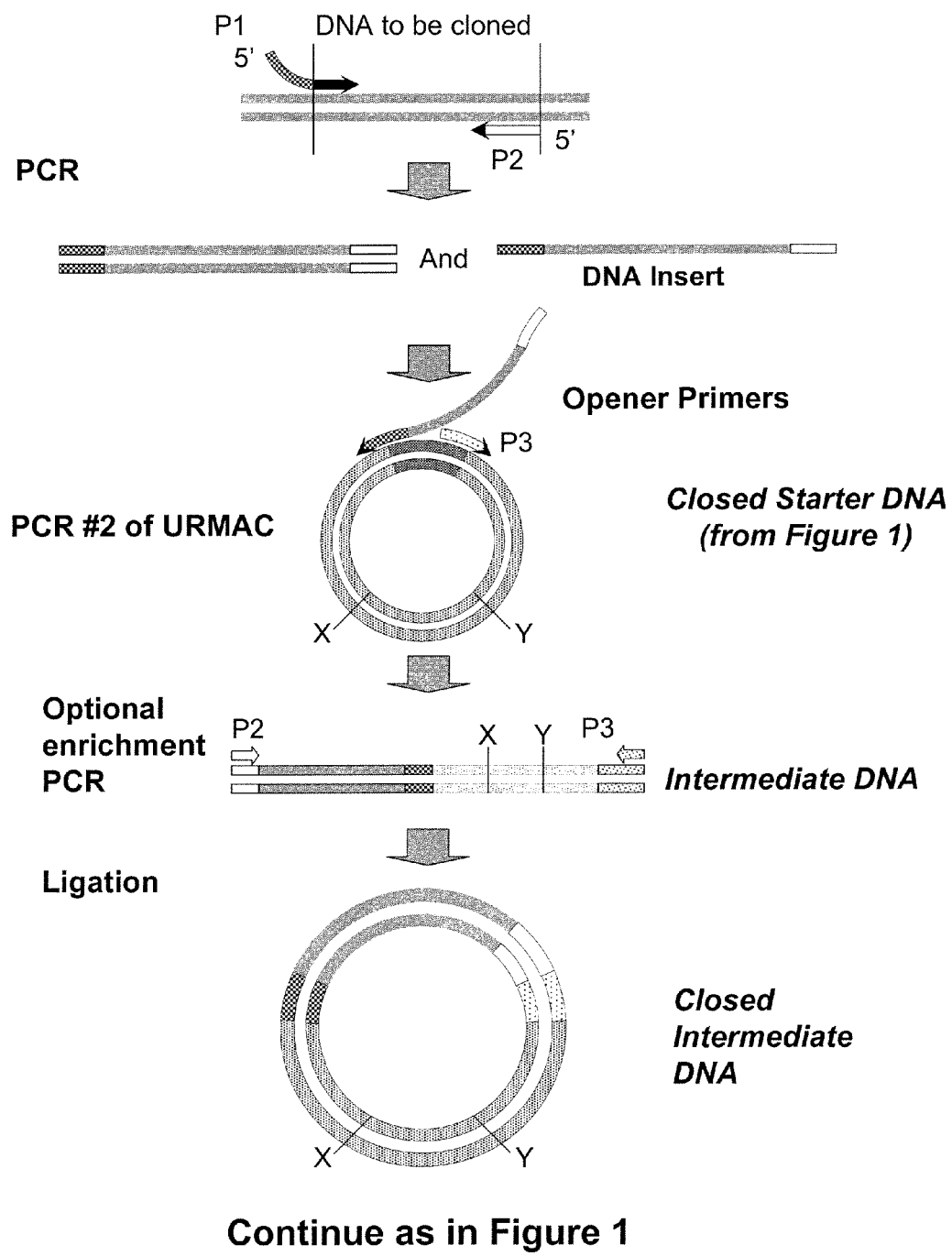
FIG. 5 depicts the URMAC methods used to generate three M2 deletion replicon constructs, as described in Example 1, below.

The URMAC method was used to delete the M2-1 and M2-2 ORFs from the RSV replicon plasmid, generating ΔM2-1, ΔM2-2, and ΔM2 replicon plasmids (FIG. 5). The Starter Primers (SP1 and SP2) were designed to flank the M2 gene, producing a 2.7 kbp Starter DNA which contained the entire M2 gene, the unique upstream Xho I, and the unique downstream Aar I sites (see Table 1). Both primers were 5' phosphorylated and used with Vent polymerase (New England Biolabs) in PCR #1 according to the manufacturer's protocol at 94° C. for 2 minutes, followed by 25 cycles of 94° C. for 20 seconds, 53° C. for 30 seconds, and 72° C. for 3 minutes, followed by incubation at 72° C. for 5.5 minutes, and storage at 4° in a GeneAmp 2700 thermocycler. PCR #1 produced the 2.7 kbp Starter DNA. All synthetic oligonucleotide primers used in this study were obtained commercially (Integrated DNA Technologies, Inc.)

The PCR #1 reactions were removed from the thermocycler immediately after the tubes reached 4° C. to avoid possible exonuclease activity that would damage the termini and inhibit ligation. The Starter DNA was then purified on a spin column according to the manufacture's instructions. The ends of purified Starter DNA were self-ligated (Ligation #1) using T4 ligase (Invitrogen), according to the manufacture's protocol, overnight at 14° C. to produce the Closed Starter DNA.

The Closed Starter DNA was subjected to a second round of amplification (PCR #2), using 4 Opener Primers (OP) in different combinations, paired to generate each of the three desired deletions (FIG. 5), and Pfu Turbo polymerase (Stratagene) according to the manufacturer's protocol at 95° C. for 2 minutes followed by 25 cycles of 95° C. for 20 seconds, 51° C. for 30 seconds and 72° C. for 3 minutes, followed by 72° C. for 10 minutes, and the samples were stored at 4° C. For deletion of the M2-1 ORF, OP1 and OP2 flanked the M2-1 ORF in the inverted orientation. OP2 was situated in the M2-1/M2-2 overlap region to maintain the M2-2 start codon, producing a 2.1 kbp linear Intermediate DNA. For the deletion of the M2-2 ORF, OP3 and OP4 were designed to flank the M2-2 ORF in the inverted orientation, producing a 2.4 kbp Intermediate DNA. To delete the entire M2 gene, OP1 and OP4 were used, producing a 1.8 kbp Intermediate DNA. The PCR #2 reactions were removed from the thermocycler immediately after the tubes reached 4° C. to avoid exonuclease activity that would damage the termini and inhibit ligation. The Intermediate DNA was then purified by Qiagen QIAquick PCR Purification Kit columns according to the manufacture's instructions. Each of these Intermediate DNAs was then self-ligated using T4 ligase (Ligation #2) (Invitrogen), according to the manufacture's protocol, overnight at 14° C. to generate Closed Intermediate DNAs.

The three Closed Intermediate DNAs were then amplified by a third round of PCR (PCR #3), using SP1 and SP2 primers from PCR #1 and Pfu Turbo polymerase at 95° C. for 2 minutes followed by 25 cycles of 95° C. for 20 seconds, 53° C. for 30 seconds, 72° C. for 3 minutes, followed by 72° C. for 10 minutes, and the sample was stored at 4° C. The resulting three Linear Modified DNAs were digested with Xho I (New England Biolabs) and Aar I (Fermentas), as was the parental, replicon plasmid, MP312. The digested DNAs were purified by electrophoresis on SeaKem (BioWhittaker Molecular Applications) agarose gels. Appropriate fragments were excised from the gels and purified using the Qiagen gel purification kit according to the manufacturer's protocol. The Linear Modified DNAs were separately ligated into the replicon plasmid, resulting in three Modified Original DNA Plasmids, RSV replicon plasmids with deletions of: M2-1 ORF (ΔM2-1); M2-2 ORF (ΔM2-2); and both ORFs (ΔM2).

ElectroMax 10Dβ *E. coli* cells (Invitrogen) were electroporated with 5 μl of each of the three Mutant Plasmids, diluted 1:5 in distilled water. For transformation, a BioRad Gene Pulser II was used under the following conditions: 2.5 V, 25 Faradays and 100Ω. Cells were then resuspended in 800 μl SOC media of which 200 μl was plated on tetracycline containing LB agar plates and incubated for 48 hours at 33° C.

To identify plasmids with the proper deletions, colonies of the transformed bacteria were picked from plates and grown overnight in 5 ml of YT broth containing 10 μg/ml tetracycline. DNA was extracted from 1 ml of the mini-cultures using the Qiagen miniprep kit according the manufacturer's protocol. Minipreps were screened for the proper ΔM2 fragment by PCR using primers SP1 and SP2 and PCR Supermix (Invitrogen), according to the manufacturer's protocol, 94° C. for 2 minutes, followed by 25 cycles of 94° C. for 30 seconds, 53° C. for 30 seconds, 72° C. for 3 minutes, followed by 72° C. for 5.5 minutes and the samples were stored at 4° C. PCR products were analyzed by agarose gel electrophoresis. Mini-cultures containing correct plasmids were used to seed 200 ml cultures. Large-scale DNA preparations were prepared with the Qiagen Maxiprep kit according the manufacturer's protocol.

Figure 6:
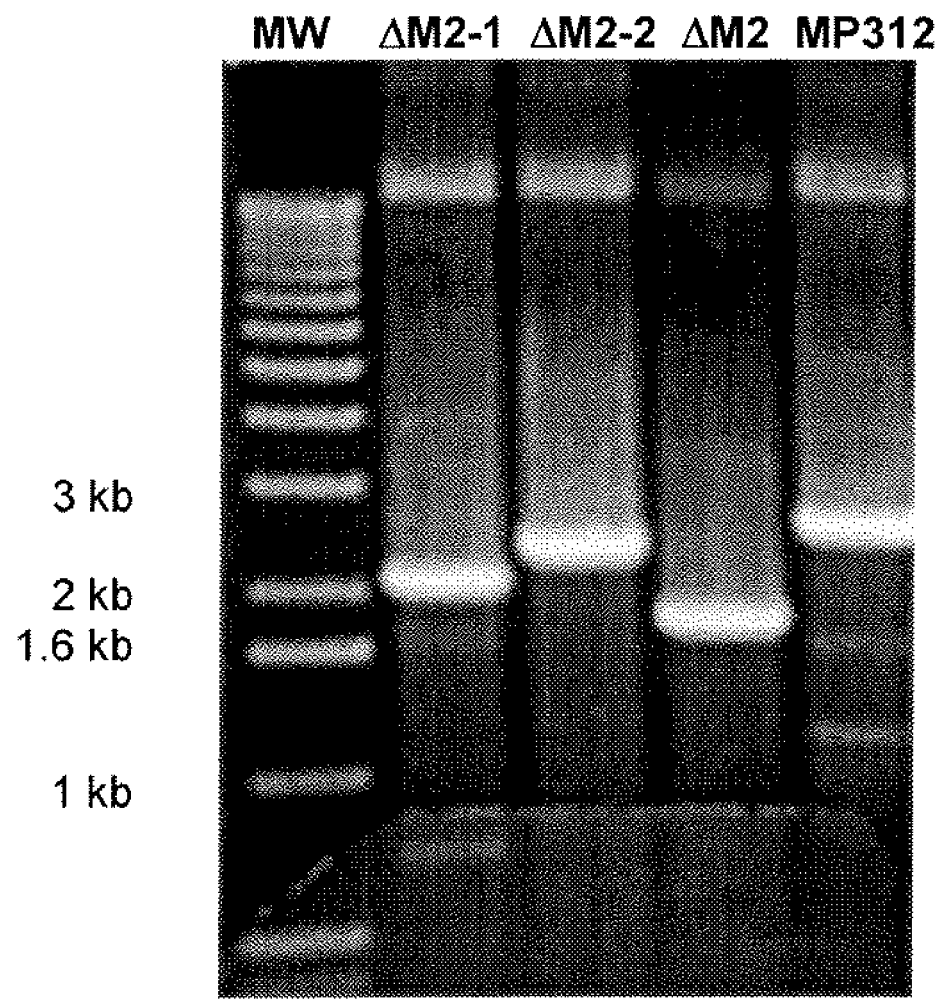
FIG. 6 depicts electrophoresis confirmation of the final replicon constructs as described in Example 1. The TDF of each replicon plasmid listed above the gel (ΔM2-1, ΔM2-2, ΔM2) was amplified by PCR using SP1 and SP2. As predicted fragment sizes were 2.1 kb, 2.4 kb, and 1.8 kb, respectively. PCR of MP312, the parental replicon plasmid, containing the entire M2 gene, the original TDF, is 2.6 kb.

The deletions in the maxipreps of the three Mutant Plasmids were confirmed by PCR with the SP1 and SP2 Starter Primers (FIG. 6). The size of the fragment amplified from all three constructs was correct. Maxipreps were then sequenced to confirm that the deletions were precise, using the Big Dye Terminator v.1.1 Cycle Sequencing kit (Applied Biosystems) and the ABI 3700 sequencer. The sequence between the Xho I and Aar I sites was determined to be correct for all three Mutant Plasmids. This is the only sequence that was copied and mutated during the URMAC procedures.

This study demonstrated that the URMAC technique can be used to rapidly modify large plasmids.

EXAMPLE 2

Nucleotide Deletion, Substitution and Insertion by URMAC

Figure 7B:
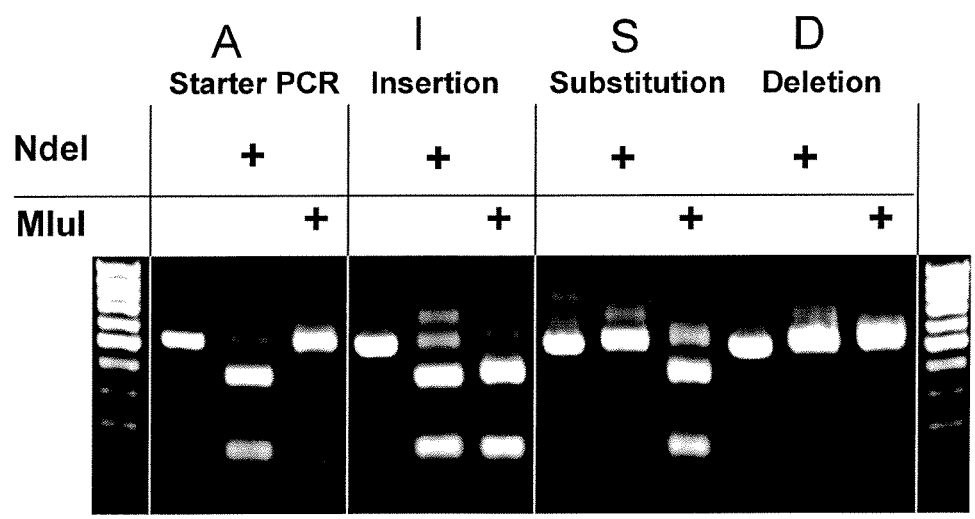
FIG. 7B depicts electrophoresis of the Linear Modified DNA after digestion with Nde I or Mlu I restriction enzymes to confirm that the mutations were successful using the URMAC methods. This figure is contemplated for inclusion in an URMAC kit of the invention. The package insert describes positive controls for nucleotide insertion, substitution or deletion as described in Example 2.

FIG. 7A-B sets out results of three URMAC experiments which respectively deleted, substituted or inserted nucleotides in the Modification Target of pUC18 plasmid, followed by verification of the three URMAC results by restriction digestion. These protocols are also set out at the end of this example. In these Experiments (FIG. 7A, upper panel), URMAC Starter DNA was generated during the first PCR (PCR #1) reaction. This reaction contained: Template: 1 µl (100 pg) pUC18 plasmid, Primers: 1.5 µl total (75 pmol of each "Starter Primer"), thermostable DNA polymerase and corresponding PCR buffer mix: 22.5 µl, in a total reaction volume of 25 µl. One µl of the PCR product was loaded on 1% agarose gel and stained with ethidium bromide (5 ng/ml). The results are shown in FIG. 7A, upper panel. The Starter DNA was self-circularized in a ligation reaction (first ligation reaction). The ligation reaction contained: Starter DNA 1 µl from the Starter PCR reaction, T4 DNA ligase and buffer. The reaction was incubated at room temperature for 10 minutes then heat inactivated at 65° C. for 10 minutes. This ligation step results in the formation of the Closed Starter DNA.

In the second set of URMAC PCR reactions (FIG. 7A, middle panel), an Mlu I site was inserted adjacent to the native Nde I site in the Modification Target of pUC18 plasmid without affecting the Nde I site (I); an Mlu I site was inserted in place of the native Nde I site which results in substitution (S) of the 6 nucleotides that makes up the Nde I site with 6 nucleotides that make up the Mlu I site; or the native Nde I site was deleted (D). The second set of PCR (Mutagenic PCR) reactions included one µl from the first ligation reaction as the template (or a dilution of the first ligation; 1:2 to 1:200), Primers: 1.5 µl total (75 pmol of each mutagenic "Opener Primer"), thermostable DNA polymerase and corresponding PCR buffer mix: 22.5 µl for a total reaction volume of 25 µl. This set of PCR reactions produced the Intermediate DNA of insertion, substitution or deletion. One microliter was loaded on a 1% agarose gel and the results are shown in FIG. 7A, middle panel. The Intermediate DNA products were self-ligated in separate ligation reactions (ligation #2). Each ligation reaction contained: Intermediate DNA 1 µl, T4 DNA ligase and buffer. The reactions were incubated at room temperature for 10 minutes then heat-inactivated at 65° C. for 10 minutes. This ligation step resulted in the formation of the Closed Intermediate DNA.

In the last and optional enrichment set of PCR reactions (FIG. 7A, lower panel), the Starter Primers were used to generate the Linear Modified DNA. Each PCR reaction in this set contained: one pi from the second ligation reaction as the template, Primers: 1.5 µl total (75 pmol of each Starter Primer), thermostable DNA polymerase and corresponding PCR buffer mix: 22.5 µl, for a total reaction volume of 25 µl. One microliter of the final URMAC product was loaded on a 1% agarose gel and the results are shown in FIG. 7A, lower panel.

In these experiments, pUC18 (Roche Applied Science, Indianapolis, Ind.) was used as the Original DNA.

Confirmations of successful mutagenic insertion, substitution and deletion in the control URMAC reactions that use pUC18 as template are shown in FIG. 7B. A 2 µl aliquot from each final URMAC PCR product was digested at 37° C. for 60 minutes with: Nde I, which cuts once, except when the Nde I site was replaced by substitution (S) or deletion (D); Mlu I, which cuts at the inserted (I) Mlu I sequence, and at the substituted (S) Mlu I sequence. The total volume of each digestion reaction was 10 µl. Four µl from each digestion reaction were loaded in individual wells of a 14-well agarose gel. DNA size markers were included at the first and last lanes of the gel for DNA size comparison.

The text below is an example of a package insert for an URMAC kit of the invention wherein the three experiments are to be used as control experiments. The control experiments serve to demonstrate to the person using the kit that the protocols are being properly carried out and the reactions are proceeding as intended.

UnRestricted Mutagenesis And Cloning (URMAC) is a set of molecular biology methods designed to make site-directed DNA mutations and to clone DNA sequences by biochemical means. It replaces all traditional subcloning and mutagenesis steps except for the insertion of the modified DNA into final plasmid.

While URMAC can be adapted to work with a variety of DNA sizes, this kit has been optimized to work with DNA sequences up to 50 kbp in size. A control target and primers are included to verify the URMAC procedure in your laboratory.

Pre-URMAC Preparation:
1. Locate two unique restriction sites that flank your desired mutation site. These restriction sites will be used at the end, to insert your final URMAC product into your original plasmid.
    a. In the control URMAC reaction (included in the kit), the two unique restriction enzyme sites chosen to flank the mutation area in pUC18 are Pfo I at position 47 and Eco RI at position 451. The distance between these two sites is 404 bp.
    b. In the provided standard control pUC18 plasmid, the mutation site is the 6 nucleotides that make up the Nde I restriction site. This Nde I site at position 185 will be the target for deletion, substitution, or insertion.
2. Design a good primer pair (using a software program) that would amplify a stretch of DNA that includes the target sequence and both unique flanking restrictions sites. These primers are known as Starter Primers (SP).
    a. In the control URMAC, SP1 and SP2 will produce a 531 bp product.
3. Design a Mutagenic Primer (MP) pair. The 3' ends of these two primers should face away from each other. The ends of the PCR product generated by these primers will be ligated, so these primers should include all the nucleotide that you want in the final construct.
    a. For deletion, design the primers to flank the target nucleotide or sequence that you wish to delete.
       The control URMAC deletion primers are:
          D>, with its 5' end just downstream of Nde I
          D<, with its 5' end upstream of Nde I.
    b. For insertion, add the nucleotides you wish to insert at the 5' end of one or the other of the MP (or some to one and some to the other).
       The control URMAC insertion primers are:
          I>, containing 3 nucleotides of the Mlu I site, without affecting the Nde I site
          I<, containing the other 3 nucleotides of the Mlu I site.
    c. For substitution, choose the location of the primer such that amplification would delete the sequence you wish to remove, then add your desired insertion sequence to the 5' end of one or the other MP (or some to one and some to the other).
       The control URMAC substitution primers are positioned as described for the deletion primers, with 5' extensions as described for the insertion primers:
          S>, with 3 nucleotides of the Mlu I site added to its 5' end
          S<, with the other 3 nucleotides of the Mlu I site added to its 5' end.
4. Synthesize both primer pairs (using primer manufacturer of your choice), SP and MP, with phosphorylated 5' ends.

5. Dissolve the primers in water (100 pmol/μl). Store frozen at −20° C.
6. Dilute target plasmid DNA, keep the amount of starting plasmid DNA to a minimum. As a general guideline, use 100 picograms of DNA for every 3-5 kbp of plasmid. If your plasmid size is 20 kbp, use 0.6 ng of starting template.

The URMAC Protocol:

Store the kit in a non-frost-free freezer at −20° C. Quickly remove and thaw only the required tubes from the kit to do one mutagenesis step at a time. Perform a control PCR at the same time using the provided pUC18 plasmid and control primers to assure that the kit is working properly.

1. Starter PCR (1st PCR)
    a. 1 PCR tube (yellow) containing premixed PCR components.
    b. Add 1 μl of your diluted plasmid (~30 pg of DNA/kbp of plasmid).
    c. Add 1.5 μl of the SP mix (equal volumes of your SP stocks)
    d. Place PCR tube in a thermocycler and start the 1st PCR. The following conditions work well for the control URMAC. The control URMAC will also work with most conditions you chose for your target mutagenesis:
        i. Initial: 94° C. 2 min
        ii. 20 cycles:

| | |
|---|---|
| 94° C. | 20 sec |
| 60° C. | 30 sec (Use manufacturer's calculated Tm) |
| 68° C. | 1 min (1 min/kb PCR product) | iii. Final: 68° C. 5 min

Note that the annealing temperature and the extension time are critical parameters for successful PCR. Since the amount of mono and divalent ions in our PCR buffer is not necessarily the same as that of your primer design software, we recommend using the primer manufacturer's melting temperature (Tm) as your annealing temperature. Lowering this parameter may result in no PCR product or a product with multiple bands.

2. First Ligation
    a. Add 1-5 μl of your first PCR to one blue tube, containing the URMAC circularization mix. Vortex well. No need to add water. Our circularization buffer has a wide dynamic range.
    b. Incubate 10 min at room temperature. If your PCR product size is above 1 kbp, increase this time by 5 min per kbp.
    c. Heat inactivate at 65° C. for 10 min. Do not skip this step.
3. Mutagenic PCR (2nd PCR)
    a. Add 1 μl from the first ligation reaction (or a dilution of this reaction: see Note 2, below; 1:200 for the control reaction) to a yellow tube (contains PCR premix).
    b. Add 1.5 μl of the MP mix (equal volumes of your MP stocks).
    c. Depending the type of mutation you are performing, use the I, S, or D primers as a control.
    d. Use the same PCR conditions as for the first PCR, but change the annealing temperature to match the MPs' Tm as provided by your primer manufacturer. (Our PCR premix requires higher annealing temperature than most.)
4. Second Ligation
    a. Add 1-5 μl of your second PCR to one blue tube containing the URMAC circularization mix. Vortex well.
    b. Incubate 10 min at room temperature. If your PCR product size is above 1 kbp, increase this time by 5 min per kb.
    c. Heat inactivate at 65° C. for 10 min. Do not skip this step.
5. Final PCR
    a. Transfer 1 μl of your second ligation reaction (or a dilution of this reaction: see Note 2, below) into a yellow PCR tube (contains PCR premix).
    b. Add 1.5 μl of SP mix (as used in the 1st PCR).
    Use the same PCR conditions that were used in the 1st PCR, but increase the number of cycles to 30. Should you need more of this final product, repeat this step.

Post URMAC

Digest your final URMAC product with the enzymes selected in Step 1, and insert it into your original plasmid, similarly digested.

Notes:
1. Because the URMAC DNA sequences are usually short, PCR generally produces more than enough DNA for enzymatic digestion, purification, and cloning.
2. A quick agarose gel analysis of your product following each PCR can inform modifications to the protocol. If there is a large amount of product, add 1 μl of product to the ligation, then dilute the ligation before the next PCR. If there is low yield, add more than 1 μl (up to 5 μl) of product to the ligation reaction. If there is no product from a PCR reaction, repeat the reaction with altered parameters such as more or less template.
3. If amplifying a short PCR product as in the control URMAC, so much product may be made in the 1st PCR that it is carried over into the Final PCR. To avoid this problem, dilute the ligation reaction. Successful 1st PCR followed by a good ligation can be diluted up to $10^{-5}$ without affecting the amount of product from the 2nd PCR. Generally, 1:200 dilution of the 1st ligation reaction works well.
4. The amount of PCR product needed for the ligation steps depends on the amount of specific PCR product added to the ligation. Generally 1-5 μl work well. 1 μl is the preferred amount when the PCR reactions produce a good yield.
5. Note that none of the URMAC steps require DNA purification even when the 1st or the 2nd PCR products show bands in addition to the correct one. Usually the last PCR results in a single band when resolved by agarose gel electrophoresis.
6. Control Primers:

SP1
(SEQ ID NO: 7)
5'-Phos-ACACATGCAGCTCCCGGAGA, position 35-45 on pUC18

SP2
(SEQ ID NO: 8)
5'-Phos-CTCACTCATTAGGCACCCCAGG, pos. 545-566 on pUC18

D>
(SEQ ID NO: 9)
5'-Phos-CGGTGTGAAATACCGCACAGAT

D<
(SEQ ID NO: 10)
5'-Phos-GTGCACTCTCAGTACAATCTGC

```
S>
                                                  (SEQ ID NO: 11)
5'-Phos-CGTCGGTGTGAAATACCGCACA S<
                                                  (SEQ ID NO: 12)
5'-Phos-CGTGTGCACTCTCAGTACAATC I>
                                                  (SEQ ID NO: 13)
5'-Phos-CATATGCGGTGTGAAATACCGCAC I<
                                                  (SEQ ID NO: 14)
5'-Phos-ACGCGTGTGCACTCTCAGTACAAT
```

EXAMPLE 3

URMAC Using OIL Starting Primers

Figure 1:
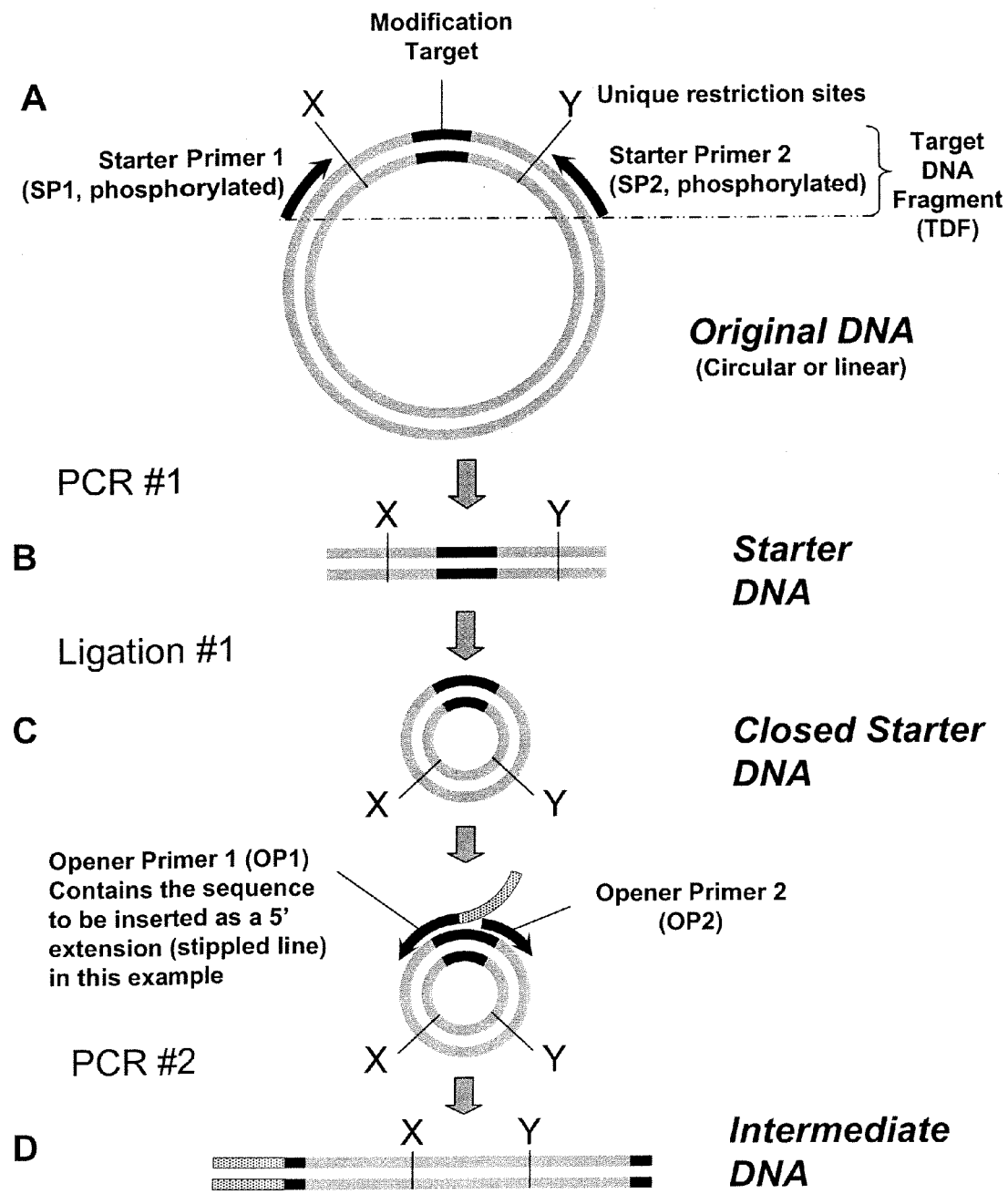
FIG. 1 illustrates the steps in the unrestricted mutagenesis methods (URMAC).
Figure 2:
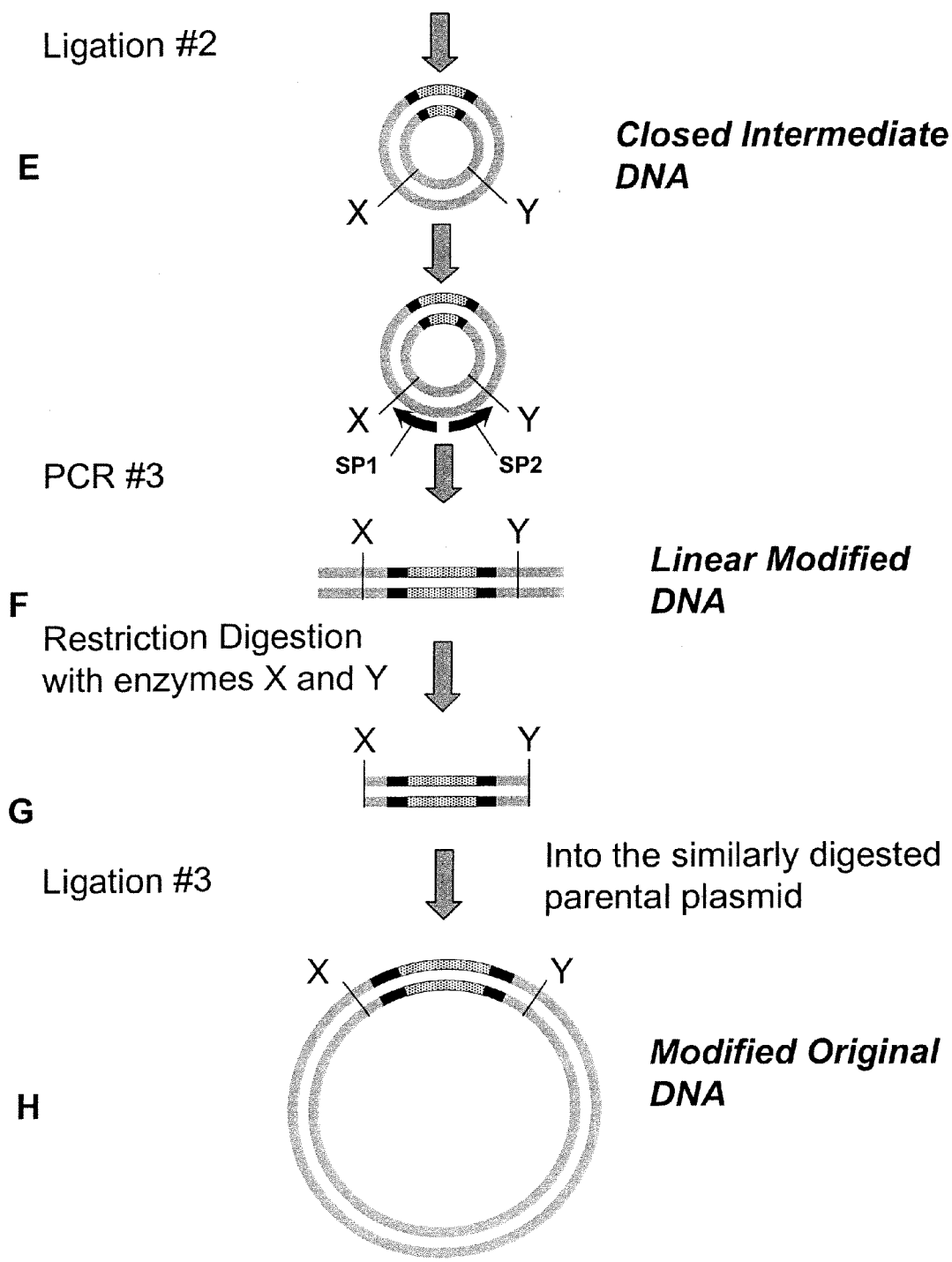
FIG. 2 illustrates URMAC cloning of any size Insert DNA by blunt-end ligation to the Intermediate DNA. The Intermediate DNA is amplified in PCR1 from the Closed Starter DNA of the URMAC technique, and an Insert DNA is amplified in PCR #2. Both the Intermediate DNA and the Insert DNA will have blunt ends if they are produced by a high-fidelity thermostable polymerase such as Vent or Pfu. Alternatively, an Insert DNA with blunt ends generated by restriction digestion or another method can be used in this technique. The Insert DNA will not be directionally cloned into the Intermediate DNA because the ends are not unique. To select molecules with the correct Insert DNA orientation, two primers, one from PCR1 and one from PCR2, that hybridize to adjacent DNA sequences on opposite strands are used in PCR3 to amplify the Closed Intermediate DNA. Only a molecule with the Insert DNA in the correct orientation will be amplified. This DNA is self-ligated to form the Closed Intermediate DNA, and the URMAC technique is continued to completion to generate a Modified Original DNA containing the Insert DNA.
Figure 3:
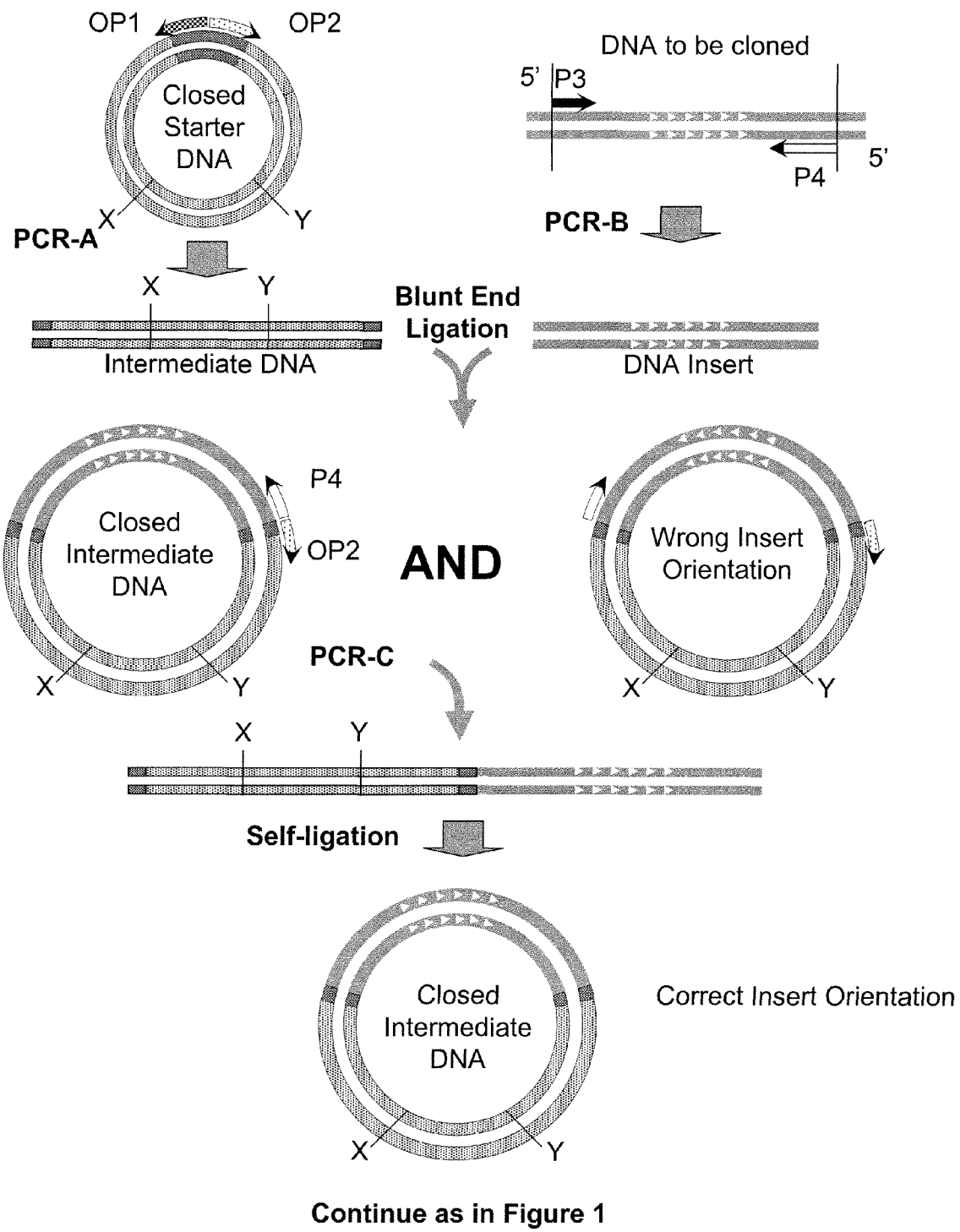
FIG. 3 illustrates URMAC cloning by ligating a DNA of interest into the Intermediate DNA. Unique restriction sites (R and/or N) are incorporated into one or both Opener Primers. The same restriction sites are also incorporated into the flanking regions of any DNA of interest by amplifying this DNA by PCR, or by using a DNA that contains these restriction sites. After the second PCR step (PCR #2 of URMAC), the PCR products and the flanking region of the DNA of interest are digested with the restriction enzymes that recognize the newly added restriction sites. The resulting products are purified and ligated together to generate the Closed Intermediate DNA. Subsequent steps are the same as in the basic URMAC methods.
Figure 4:
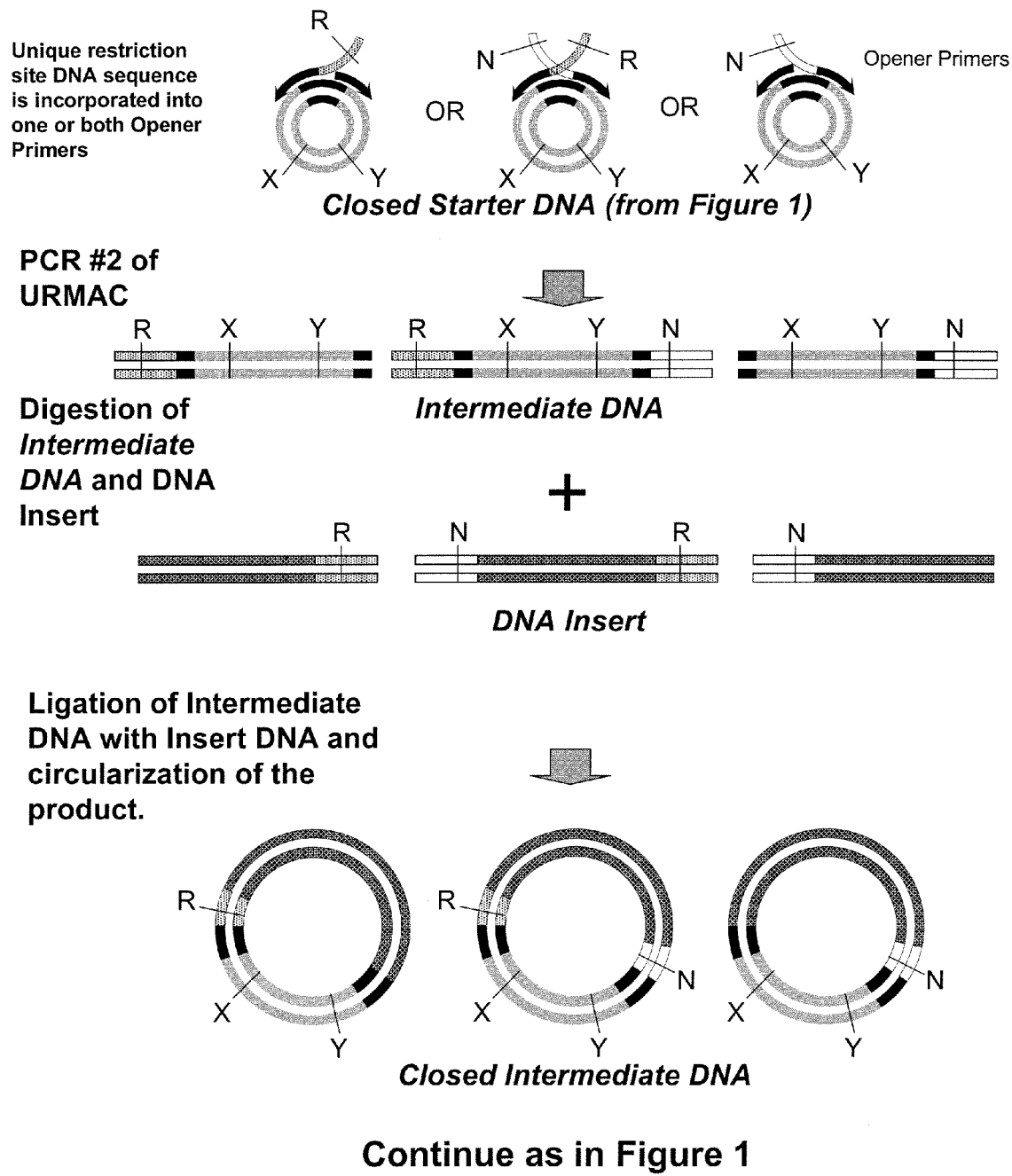
FIG. 4 illustrates URMAC cloning using a large primer. The DNA to be inserted is amplified by PCR, using two primers P1 and P2. One of the primers, P1, is designed to contain a 5' extension that is complementary to the Modification Target region on the Closed Starter DNA. One of the DNA strands of this PCR product, the strand that contains the P2 sequence, is used as an Opener Primer and is paired with a third primer (P3) on the Closed Starter DNA template in PCR #2 of the URMAC technique. The PCR product is the Intermediate DNA. The Intermediate DNA is then circularized by self-ligation. The subsequent steps are the same as in the basic URMAC methods. To produce free, single strand Insert DNA-containing primer for use in PCR #2, the initial PCR reaction may contain more primer P2 than P1, resulting in preferential production of the needed primer strand. An optional step, enrichment for the Intermediate DNA, may be performed by PCR, using the P2 and P3 primers.

A version of URMAC was carried out using primers named "Oligo Instead of Ligation" (OIL) primers. The OIL primers do not need to be phosphorylated and the number of thermocycles can be significantly reduced for the first PCR from 20-30 cycles to only 10 cycles. When the primers are used, no ligation is required between the first and second URMAC PCR reactions. For the second PCR reaction, the Opener Primers are added directly to the first PCR reaction, or to a small portion of the first PCR reaction, and the second PCR reaction is performed for an additional 20-30 cycles. The Opener Primers do not serve to "open" any DNA because their template is already linear. During the second PCR reaction the Opener Primers are extended and one half of the Starter DNA is amplified from each, terminating with a copy of the 5' OIL extension added to the Starter Primers in the first PCR. The 3' termini of these product molecules can then hybridize and extend, completing the Intermediate DNA (See FIG. 8). The Intermediate DNA is then self-ligated to produce the Closed Intermediate DNA and the URMAC method is continued, as shown in FIG. 1.

The method introduced a Mlu I restriction site into pUC18 adjacent to the unique Nde I site.

The Original DNA was the plasmid pUC18.

```
OIL Starter Primer A
                                                  (SEQ ID NO: 15)
  5'-cttacgggctagaggatgacACACATGCAGCTCCCGGAGA OIL Starter Primer B
                                                  (SEQ ID NO: 16)
  5'-gtcatcctctagcccgtaagCTCACTCATTAGGCACCCCAGG
```

The lower case, unbolded nucleotides are the 5' OIL extensions in this example. The OIL extensions are complementary. These OIL Starter Primers are used in the first and the final PCR reactions. The OPs for the second PCR reaction introduce an Mlu I restriction enzyme site (underlined in sequence below).

```
Opener Primer A
5'-Phos-CATATGCGGTGTGAAATACCGCAC    (SEQ ID NO: 13)

Opener Primer B
5'-Phos-ACGCGTGTGCACTCTCAGTACAAT    (SEQ ID NO: 14)
```

Figure 9:
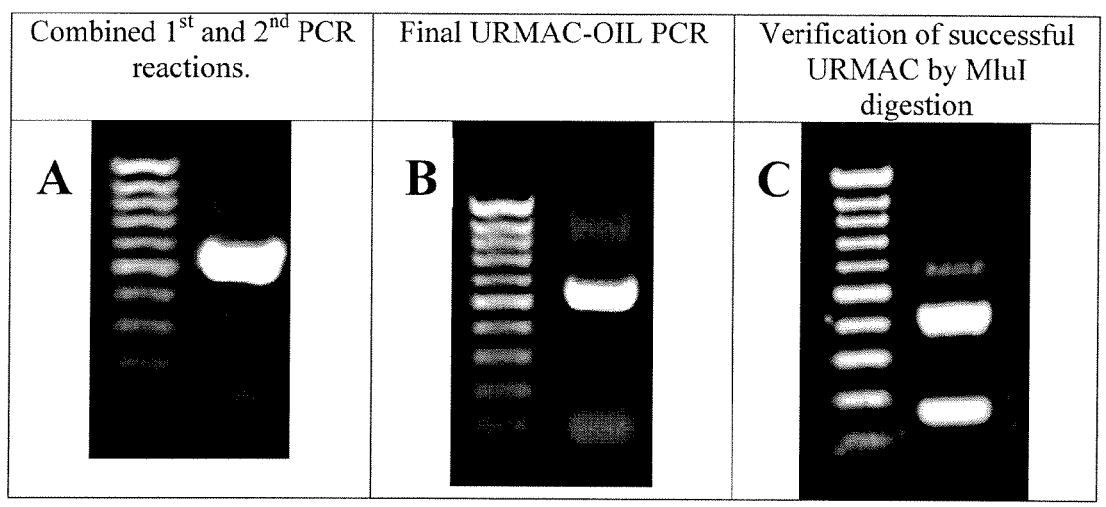
FIG. 9 depicts the results from URMAC performed with the OIL Starter Primers to insert an Mlu I restriction site in pUC18, as described in Example 3. OIL SPA and OIL SPB were used at a low concentration (1 picomole/25 μl reaction) for 10 cycles followed by the addition of the two Opener Primers at normal concentrations (75 picomole/25 μl reaction) followed by another 25 thermal cycles. The Intermediate DNA product is shown in panel A. The Intermediate DNA was self-ligated and amplified with OIL SPA and OIL SPB in the final PCR to produce the Linear Modified DNA, shown in panel B. The Linear Modified DNA contained the inserted Mlu I restriction site as demonstrated by Mlu I digestion in panel C.

URMAC was performed using the OIL Starter Primers SPA and SPB at 1 picomole/25 µl reaction for 10 thermal cycles followed by the addition of Opener Primers at 75 picomoles/25 µl reaction and another 25 thermal cycles (FIG. 9A). The final PCR was performed using SPA and SPB as described for the basic URMAC method (FIG. 1). This final PCR product is shown in FIG. 9B.

The final product was tested for the insertion of the Mlu I site in the pUC18 control plasmid by restriction digestion. The final product did contain an insertion of the Mlu I site, as shown in FIG. 9C.

---

We claim:

1. A method of modifying a nucleic acid, comprising the steps of: contacting an Original DNA, comprising a Target DNA Fragment having a Modification Target flanked by two restriction sites, with a DNA polymerase and two Starter Primers selected for amplifying the Target DNA Fragment, such that the Starter Primers anneal to segments of the Original DNA at the ends of the Target DNA Fragment; amplifying, with the Starter Primers, a portion of the Original DNA comprising the Target DNA Fragment, generating a Starter DNA; self-ligating the Starter DNA with a DNA ligase, forming a Closed Starter DNA; contacting the Closed Starter DNA with a DNA polymerase and two Opener Primers selected for causing a modification within the Target DNA Fragment, such that the Opener Primers anneal to opposite strands of the double stranded Target DNA Fragment such that the 5' ends of the Opener Primers are proximal and the 3' ends are distal relative to each other; amplifying the Closed Starter DNA with the Opener Primers, generating an Intermediate DNA; and forming the modified nucleic acid by the steps of: self-ligating the Intermediate DNA with DNA ligase, forming a Closed Intermediate DNA; and, optionally, amplifying the Closed Intermediate DNA by contacting the Closed Intermediate DNA with the Starter Primers and a DNA polymerase, generating a Linear Modified DNA containing the modification.

2. The method of claim 1, further comprising the steps of: digesting the product of claim 1 and the Original DNA with restriction enzymes corresponding to the restriction sites flanking the Modification Target, generating a Modified DNA fragment and an Original DNA fragment, respectively; purifying the generated DNA fragments; and ligating the Modified DNA fragment and the Original DNA fragment to generate a Modified Original DNA.

3. The method of claim 2, further comprising the step of: selecting clones of the Modified Original DNA that contain the Modified DNA in the correct orientation.

4. The method of claim 2, further comprising the steps of: removing an additional adenine residue present at the ends of the product of claim 1 that is due to the DNA polymerase, by exonuclease treatment to generate blunt ends; treating the Original DNA with a blunt restriction enzyme; purifying the treated DNA fragments; ligating the treated DNA with DNA ligase; and selecting clones of the Modified Original DNA that contain the modified DNA in the correct orientation.

5. The method of claim 1, wherein the modification is at least one nucleotide DNA insertion.

6. The method of claim 1, wherein the modification is at least one nucleotide substitution.

7. The method of claim 1, wherein: the modification is a DNA insertion and the DNA Insert is amplified by PCR using two primers with one of the primers having a 5' extension complementary to the Closed Starter DNA; the strand of the amplified DNA Insert that is complementary to the 5' primer extension is used as an Opener Primer so that the 5' extension creates a 3' extension complementary to the Closed Starter DNA; and the Opener Primer is paired with a second Opener Primer to generate the Intermediate DNA, so that the second Opener Primer comprises a sequence that is complementary to adjacent portions of the Closed Starter DNA having no intervening nucleotides.

8. The method of claim 7, wherein each Opener Primer comprises a sequence generated by PCR and both sequences are thereby inserted into the Intermediate DNA.

9. The method of claim 7, wherein the primers that amplify the DNA Insert are used in unequal amounts to generate more of the DNA strand with the 3' extension complementary to the Closed Starter DNA.

10. The method of claim 1, wherein: the modification is a DNA insertion; wherein the DNA Insert and the Intermediate DNA are amplified with a DNA polymerase that generates blunt ends on PCR products; the method further comprises the steps of: blunt end ligating the DNA Insert and the Intermediate DNA to generate the Closed Intermediate DNA; and selecting a Closed Intermediate DNA in the correct orientation by PCR amplification with two primers, so that one primer is selected for amplifying the Intermediate DNA and the other primer is selected for amplifying the DNA Insert, so that both primers anneal to adjacent segments of the Closed Intermediate DNA having no intervening nucleotides and anneal to opposite strands of the Closed Intermediate DNA.

11. The method of claim 10, further comprising the step of: removing an additional adenine residue, present at the ends of the PCR product DNA due to the DNA polymerase, by exonuclease treatment to generate blunt ends.

12. The method of claim 2, wherein the modification is an insertion of at least one unique restriction site and the method further comprises the steps of: digesting the Modified Original DNA and a DNA Insert with the unique restriction enzymes corresponding to the unique restriction sites inserted into the Modified Original DNA; purifying the fragment of the Modified Original DNA and a fragment of the DNA Insert; and ligating the fragment of the Modified Original DNA and a fragment of the DNA Insert to generate the Modified Original DNA containing the DNA Insert.

13. The method of claim 1, wherein: the product of claim 1 comprises regions that are homologous to the Original DNA, the homologous regions flanking the Modification Target; and the product of claim 1 and the Original DNA are joined by homologous recombination.

14. The method of claim 13, wherein the homologous recombination is enhanced by recombineering.

15. The method of claim 1, further comprising the steps of: starting with a Closed Intermediate DNA; and treating the Closed Intermediate DNA as the Closed Starter DNA and using different Opening Primers, repeating the steps of: contacting the Closed Starter DNA with a DNA polymerase and two Opener Primers; amplifying the Closed Starter DNA with the Opener Primers, generating an Intermediate DNA; and self-ligating the Intermediate DNA with DNA ligase, forming a further Closed Intermediate DNA to generate at least one additional modification, insertion, substitution or deletion in one Modification Target region.

16. The method of claim 1, wherein the Linear Modified DNA is transcribed into Modified RNA.

17. A method of making an insertion in a nucleic acid comprising the steps of: contacting an Original DNA, which comprises a Target DNA Fragment containing a Modification Target that is flanked by two restriction sites with a DNA polymerase and two Starter Primers, the Starter Primers selected to amplify the Target DNA Fragment, so that the Starter Primers anneal to segments of the Original DNA at the ends of the Target DNA Fragment; amplifying the Target DNA Fragment using polymerase chain reaction (PCR) with the Starter Primers to generate a Starter DNA; self-ligating the Starter DNA with a DNA ligase to form a Closed Starter DNA; contacting the Closed Starter DNA with a DNA polymerase and two Opener Primers, the Opener Primers selected to insert at least one unique restriction site into the Modification Target, at least one of the Opener Primers comprising a 5' extension including at least one additional unique restriction site that differs from the restriction sites in the Target DNA Fragment, so that the Opener Primers anneal to opposite strands of the double stranded Target DNA Fragment such that the 5' ends of the Opener Primers are proximal and the 3' ends are distal relative to each other; amplifying the Closed Starter DNA using PCR with the Opener Primers to generate an Intermediate DNA; amplifying a DNA Insert with primers comprising the unique restriction sites that differ from the restriction sites in the Target DNA Fragment; digesting the Intermediate DNA and the DNA Insert with restriction enzymes corresponding to the unique restriction sites that were added; purifying a fragment of the Intermediate DNA and a fragment of the DNA Insert; ligating the purified fragments of the Intermediate DNA and of the DNA Insert to generate Closed Intermediate DNA; and, optionally, contacting the Closed Intermediate DNA with the Starter Primers and a DNA polymerase to amplify the Closed Intermediate DNA and generate a Linear Modified DNA.

18. The method of claim 17, further comprising the steps of: digesting the product of claim 17 and the Original DNA with restriction enzymes corresponding to the restriction sites flanking the Modification Target, wherein the digestion generates a fragment of the Modified DNA and a fragment of the Original DNA; purifying the fragment of the Modified DNA and the fragment of the Original DNA; and ligating the fragment of the Modified DNA and the fragment of the Original DNA to generate Modified Original DNA.

19. A method of deleting a portion of a nucleic acid comprising the steps of: contacting an Original DNA, comprising a Target DNA Fragment containing a Modification Target that is flanked by two restriction sites, with a DNA polymerase and two Starter Primers that are selected to amplify the Target DNA Fragment, so that the Starter Primers anneal to segments of the Original DNA outside the restriction sites; amplifying a portion of the Original DNA comprising the Target DNA Fragment using polymerase chain reaction (PCR) with the Starter Primers to generate a Starter DNA; self-ligating the Starter DNA with a DNA ligase to form a Closed Starter DNA; contacting the Closed Starter DNA with two Opener Primers and a DNA polymerase, so that the Opener Primers anneal to segments of the DNA separated by intervening nucleotides flanking the intended deletion and to different DNA strands; amplifying the Starter DNA by PCR with the Opener Primers to generate an Intermediate DNA; self-ligating the Intermediate DNA with DNA ligase to generate a Closed Intermediate DNA; and, optionally, contacting the Closed Intermediate DNA with the Starter Primers and DNA polymerase to amplify the Closed Intermediate DNA and generate a Linear Modified DNA containing the deletion.

20. The method of claim 19, further comprising the steps of: digesting the product of claim 19 and the Original DNA with restriction enzymes corresponding to the restriction sites flanking the Modification Target, wherein the digestion generates a fragment of the Linear Modified DNA and a fragment of the Original DNA; purifying the fragment of the Modified DNA and a fragment of the Original DNA; and ligating the fragment of the modified DNA and the fragment of the Original DNA to generate Modified Original DNA.

21. The method of claim 20, further comprising the steps of: repeating, using different Opener Primers, the steps of: contacting the Closed Starter DNA with two Opener Primers and a DNA polymerase, so that the Opener Primers anneal to segments of the DNA separated by intervening nucleotides flanking the intended deletion and to different DNA strands; amplifying the Starter DNA by PCR with the Opener Primers to generate an Intermediate DNA; and self-ligating the Intermediate DNA with DNA ligase to generate a Closed Intermediate DNA.

22. The method of claim 1, wherein: at least one of the amplifying steps is accomplished by polymerase chain reaction (PCR).

23. The method of claim 1, wherein: at least one of the primers is modified by phosphorylation at the 5' end.

24. The method of claim 1, further comprising the steps of: generating cohesive ends in the Linear Modified DNA and the Original DNA, by enzymes having exonuclease activity, so that the overhanging ends of the product of claim 1 contains regions that are complementary to those of the Original DNA; annealing the resulting products; and ligating by DNA ligase.

25. The method of claim 1, wherein: the Modification Target is flanked by restriction sites.

26. The method of claim 1, wherein the modification is at least one nucleotide deletion.

27. The method of claim 1, wherein the modification is one of the following: at least one nucleotide insertion combined with at least one nucleotide substitution and at least one nucleotide deletion; at least one nucleotide insertion combined with at least one nucleotide substitution; at least one nucleotide insertion combined with at least one nucleotide deletion; and at least one nucleotide substitution and at least one nucleotide deletion.

* * * * *